United States Patent [19]

Ueda et al.

[11] 4,298,529
[45] Nov. 3, 1981

[54] ALKOXYIMINO DIOXY BUTYRIC ACID DERIVATIVES

[75] Inventors: Ikuo Ueda, Toyonaka; Takao Takaya, Kawanishi; Masakazu Kobayashi, Ikeda; Takashi Masugi, Kiltamachi; Hisashi Takasugi, Kohamanishi; Hiromu Kochi, Sakai; Tadashi Kitaguchi, Kukuchinishimachi, all of Japan

[73] Assignee: Fujisawa Pharmaceutical Co., Ltd., Osaka, Japan

[21] Appl. No.: 101,527

[22] Filed: Dec. 10, 1979

Related U.S. Application Data

[63] Continuation-in-part of Ser. No. 73,565, Sep. 7, 1979, abandoned.

[30] Foreign Application Priority Data

| Sep. 12, 1978 | [JP] | Japan | 53-112555 |
| Sep. 12, 1978 | [GB] | United Kingdom | 36564/78 |
| Jan. 12, 1979 | [JP] | Japan | 54-3106 |
| Sep. 12, 1978 | [GB] | United Kingdom | 36564/78 |
| Feb. 19, 1979 | [GB] | United Kingdom | 5791/79 |

[51] Int. Cl.$^3$ .................................... C07D 317/28
[52] U.S. Cl. .................... 260/340.9 R; 260/340.7; 260/544 Y; 544/22; 544/27; 544/28; 544/30; 562/567
[58] Field of Search .............. 260/340.9 R, 340.7, 260/544 Y; 562/567

[56] References Cited

U.S. PATENT DOCUMENTS

| 4,093,803 | 6/1978 | Cook et al. | 544/27 |
| 4,098,888 | 7/1978 | Ochiai et al. | 424/246 |
| 4,152,336 | 5/1979 | Kuroki et al. | 260/340.9 R |
| 4,152,432 | 5/1979 | Heymes et al. | 424/246 |
| 4,166,115 | 8/1979 | Takaya et al. | 424/246 |
| 4,205,180 | 5/1980 | Ochiai et al. | 560/168 |

FOREIGN PATENT DOCUMENTS 864810 9/1978 Belgium .

*Primary Examiner*—Paul M. Coughlan, Jr.
*Attorney, Agent, or Firm*—Oblon, Fisher, Spivak, McClelland & Maier

[57] ABSTRACT

The invention relates to new antimicrobially active 3-cephem compounds, processes for preparing such compounds, new intermediate compounds comprising alkoxyimino dioxy butyric acid derivatives useful in said processes, and processes for preparation of said intermediates.

7 Claims, No Drawings

ALKOXYIMINO DIOXY BUTYRIC ACID DERIVATIVES

This application is a continuation-in-part of application Ser. No. 073,565 filed Sept. 7, 1979, now abandoned.

The present invention relates to new processes for preparing antimicrobially active 3-cephem compounds. More particularly, it relates to new processes for preparing antimicrobially active 3-cephem compounds, to new intermediate compounds which are useful in said processes and to processes for the preparation thereof.

Accordingly, it is one object of the present invention to provide new processes for preparing antimicrobially active 3-cephem compounds, e.g. 7-[2-(2-aminothiazol-4-yl)-2-methoxyiminoacetamido]-3-cephem-4-carboxylic acid (syn isomer) or its pharmaceutically acceptable salt.

Another object of the present invention is to provide new intermediate compounds which are useful in said processes for preparing antimicrobially active 3-cephem compounds, e.g. 7-[2-(2-aminothiazol-4-yl)-2-methoxyiminoacetamido]-3-cephem-4-carboxylic acid (syn isomer) or its pharmaceutically acceptable salt.

A further object of the present invention is to provide processes for preparing said new intermediate compounds.

The processes included in the present invention are illustrated by the following schemes.

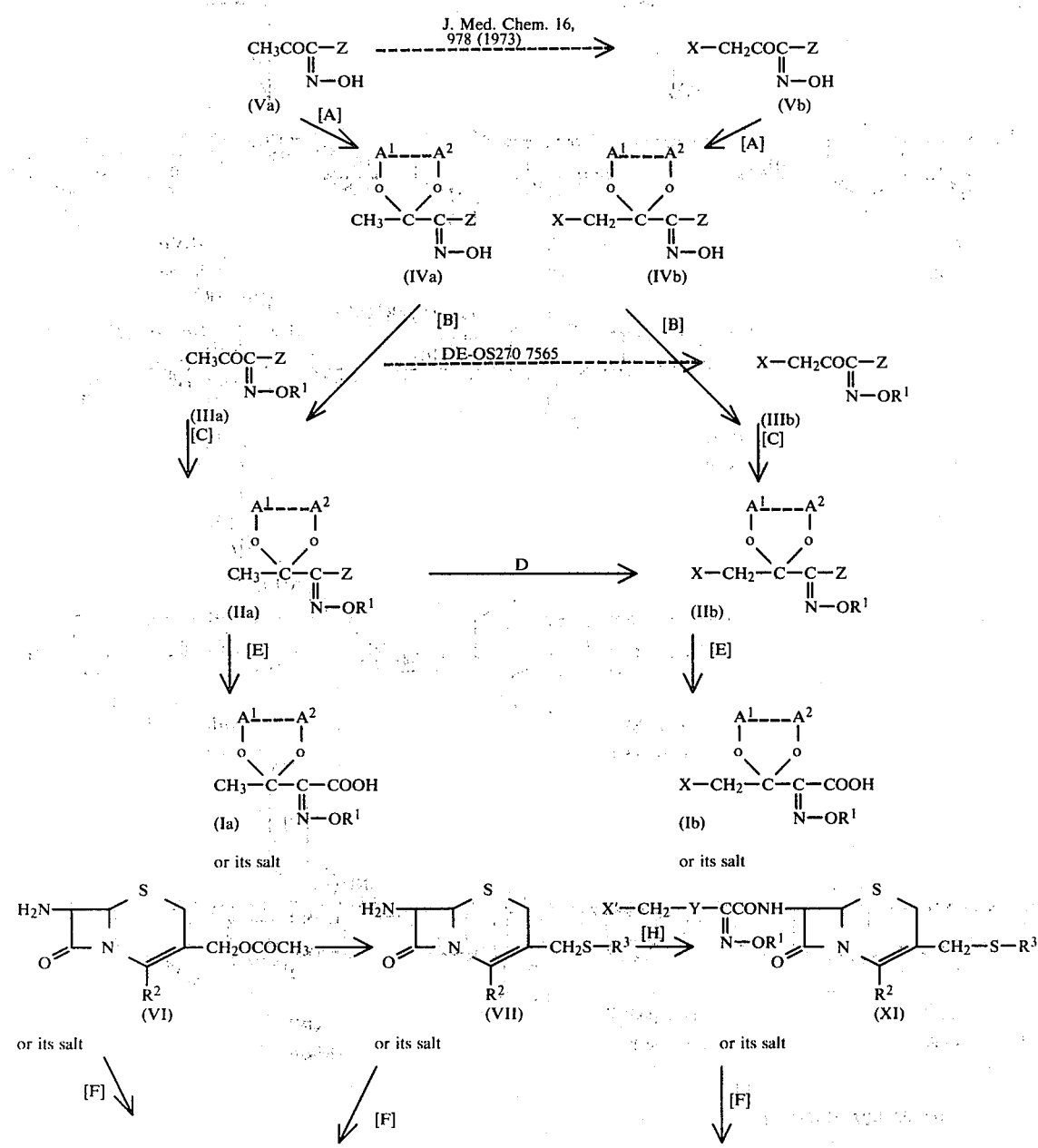

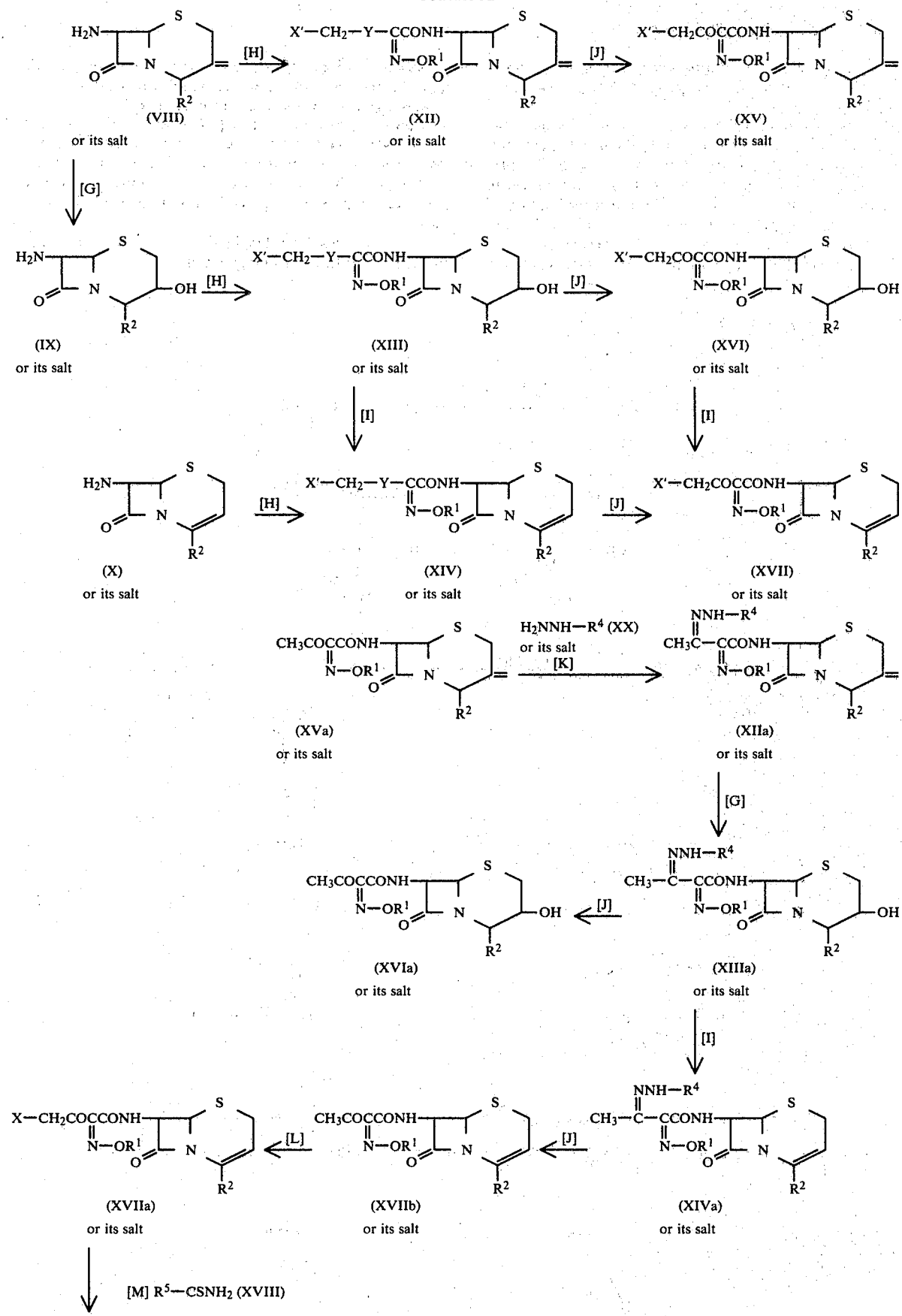
-continued

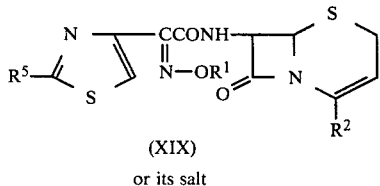

(XIX)

or its salt wherein
R[1] is an aliphatic hydrocarbon group which may have suitable substituent(s),
R[2] is carboxy or a protected carboxy group,
R[3] is a heterocyclic group which may have suitable substituent(s),
R[4] is an esterified carboxy group,
R[5] is amino or a protected amino group,
A[1] and A[2] are each an acetal residue which may be linked together,
X is halogen,
X' is hydrogen or halogen,
Y is a protected carbonyl group and
Z is an esterified carboxy group.

Among the compounds of the present invention which are useful as intermediates for preparing the highly active antibiotic compound (XIX) or its salt, preferable intermediate compounds can be illustrated by the following schemes (i) to (iii).

Scheme (i)

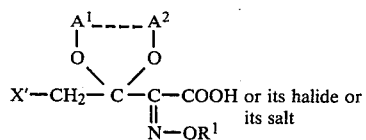

wherein R[1], A[1], A[2] and X' are each as defined above.

Scheme (ii)

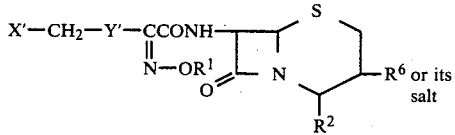

wherein R[1], R[2], X' are each as defined above, and R[6] is hydroxy, acyloxy or methylene, and Y' is carbonyl or a protected carbonyl group.

Scheme (iii)

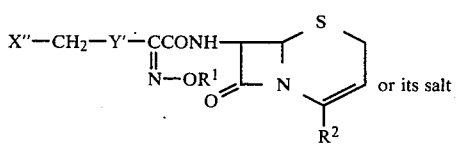

wherein R[1], R[2] and Y' are each as defined above, X" is hydrogen or halogen,
provided that X" is hydrogen when Y' is carbonyl.

The terms and definitions described in this specification are illustrated as follows.

Partial structure of the formula:

is intended to mean syn isomer.

The term "lower" is used to intend a group having 1 to 6 carbon atoms, unless otherwise provided.

"Protected carboxy group" may include an esterified carboxy group, an amidated carboxy group or the like.

Suitable examples of "ester moiety" in the "esterified carboxy group" may be lower alkyl ester (e.g. methyl ester, ethyl ester, propyl ester, isopropyl ester, butyl ester, isobutyl ester, t-butyl ester, pentyl ester, t-pentyl ester, hexyl ester, 1-cyclopropylethyl ester, etc.);

lower alkenyl ester (e.g. vinyl ester, allyl ester, etc.);

lower alkynyl ester (e.g. ethynyl ester, propynyl ester, etc.);

lower alkoxy(lower)alkyl ester (e.g. methoxymethyl ester, ethoxymethyl ester, isopropoxymethyl ester, 1-methoxyethyl ester, 1-ethoxyethyl ester, etc.);

lower alkylthio(lower)alkyl ester (e.g. methylthiomethyl ester, ethylthiomethyl ester, ethylthioethyl ester, isopropylthiomethyl ester, etc.);

halo(lower)alkyl ester (e.g. 2-iodoethyl ester, 2,2,2-trichloroethyl ester, etc.);

lower alkanoyloxy(lower)alkyl ester (e.g. acetoxymethyl ester, propionyloxymethyl ester, butyryloxymethyl ester, valeryloxymethyl ester, pivaloyloxymethyl ester, hexanoyloxymethyl ester, 2-acetoxyethyl ester, 2-propionyloxyethyl ester, etc.);

lower alkanesulfonyl(lower)alkyl ester (e.g. mesylmethyl ester, 2-mesylethyl ester, etc.);

ar(lower)alkyl, for example, phenyl(lower)alkyl ester which may have one or more suitable substituent(s) (e.g. benzyl ester, 4-methoxybenzyl ester, 4-nitrobenzyl ester, phenethyl ester, trityl ester, benzhydryl ester, bis(-methoxyphenyl)methyl ester, 3,4-dimethoxybenzyl ester, 4-hydroxy-3,5-di-t-butylbenzyl ester, etc.);

aryl ester which may have one or more suitable substituent(s) (e.g. phenyl ester, tolyl ester, t-butylphenyl ester, xylyl ester, mesityl ester, cumenyl ester, salicyl ester, etc.); an ester with a silyl compound such as tri(-lower)alkylsilyl compound, di(lower)alkylalkoxysilyl compound or tri(lower)alkoxysilyl compound, for example, tri(lower)alkylsilyl ester (e.g. trimethyl silyl ester, triethylsilyl ester, etc.), di(lower)alkylalkoxy silyl ester (e.g. dimethylmethoxysilyl ester, dimethylethoxysilyl ester, diethylmethoxysilyl ester, etc.) or tri(lower)alkoxysilyl ester (e.g. trimethoxysilyl ester, triethoxysilyl ester, etc.), or the like.

More particularly, the preferable example of ester may be nitrophenyl(lower)alkyl ester (e.g. 4-nitrobenzyl ester, 4-nitrophenethyl ester, etc.), lower alkyl ester (e.g. methyl ester, ethyl ester, propyl ester, isopropyl ester, butyl ester, isobutyl ester, tert-butyl ester, pentyl ester, neopentyl ester, hexyl ester, etc.).

"Protective group" in the "protected amino group" may include a conventional N-protective group such as acyl, substituted or unsubstituted ar(lower)alkyl (e.g. benzyl, benzhydryl, trityl, 4-methoxybenzyl, 3,4-dimethoxybenzyl, etc.), halo(lower)alkyl (e.g. trichloromethyl, trichloroethyl, trifluoromethyl, etc.), tetrahydropyranyl, substituted phenylthio, substituted alkylidene, substituted aralkylidene, substituted cycloalkylidene, or the like.

Suitable acyl may be aliphatic acyl group and acyl group containing an aromatic or heterocyclic ring. And, suitable examples of the said acyl may be lower alkanoyl (e.g. formyl, acetyl, propionyl, butyryl, isobutyryl, valeryl, isovaleryl, oxalyl, succinyl, pivaloyl, etc.), preferably one having 1 to 4 carbon atom(s), more preferably one having 1 to 2 carbon atom(s);
lower alkoxycarbonyl having 2 to 7 carbon atoms (e.g. methoxycarbonyl, ethoxycarbonyl, propoxycarbonyl, 1-cyclopropylethoxycarbonyl, isopropoxycarbonyl, butoxycarbonyl, t-butoxycarbonyl, pentyloxycarbonyl, t-pentyloxycarbonyl, hexyloxycarbonyl, etc.), preferably one having 2 to 6 carbon atoms;
lower alkanesulfonyl (e.g. mesyl, ethanesulfonyl, propanesulfonyl, isopropanesulfonyl, butanesulfonyl, etc.); aranesulfonyl (e.g. benzenesulfonyl, tosyl, etc.); aroyl (e.g. benzoyl, toluoyl, naphthoyl, phthaloyl, indancarbonyl, etc.);
ar(lower)alkanoyl (e.g. phenylacetyl, phenylpropionyl, etc.);
ar(lower)alkoxycarbonyl(e.g. benzyloxycarbonyl, phenethyloxycarbonyl, etc.); and the like.

The acyl as stated above may have 1 to 3 suitable substituent(s) such as halogen (e.g. chlorine, bromine, iodine or fluorine), hydroxy, cyano, nitro, lower alkoxy (e.g. methoxy, ethoxy, propoxy, isopropoxy, etc.), lower alkyl (e.g. methyl, ethyl, propyl, isopropyl, butyl, etc.), lower alkenyl (e.g. vinyl, allyl, etc.), aryl (e.g. phenyl, tolyl, etc.), or the like, and preferable example is mono(or di or tri)halo(lower)alkanoyl (e.g. chloroacetyl, dichloroacetyl, trifluoroacetyl, etc.)

And further, the reaction product of a silan, boron, aluminum or phosphorus compound with the amino group may also be included in the N-protective group. Suitable examples of such compounds may be trimethylsilyl chloride, trimethoxysilyl chloride, boron trichloride, butoxyboron dichloride, aluminum trichloride, diethoxy aluminum chloride, phosphorus dibromide, phenylphosphorus dibromide, or the like.

"Heterocyclic group" may be unsaturated 3 to 8-membered (preferably 5 to 6 membered) heteromonocyclic group containing 1 to 4 nitrogen atom(s), for example, pyrrolyl, pyrrolinyl, imidazolyl, pyrazolyl, pyridyl and its N-oxide, pyrimidinyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl), etc.; unsaturated condensed heterocyclic group containing 1 to 4 nitrogen atom(s), for example, indolyl, isoindolyl, indolizinyl, benzimidazolyl, quinolyl, isoquinolyl, indazolyl, benzotriazolyl, etc.; unsaturated 3 to 8-membered (preferably 5 to 6-membered) heteromonocyclic group containing 1 to 2 oxygen atom(s) and 1 to 3 nitrogen atom(s), for example, oxazolyl, isoxazolyl, oxadiazolyl (e.g. 1,2,4-oxadiazolyl, 1,3,4-oxadiazolyl, 1,2,5-oxadiazolyl, etc.) etc.; unsaturated 3 to 8-membered (preferably 5 to 6-membered) heteromonocyclic group containing 1 to 2 sulfur atom(s) and 1 to 3 nitrogen atom(s), for example, thiazolyl, thiadiazolyl (e.g. 1,2,4-thiadiazolyl, 1,3,4-thiadiazolyl, 1,2,5-thiadiazolyl, etc.), etc.; unsaturated condensed heterocyclic group containing 1 to 2 sulfur atom(s) and 1 to 3 nitrogen atom(s), for example, benzothiazolyl, benzothiadiazolyl, etc. or the like; wherein said heterocyclic group may have 1 to 2 suitable substituent(s) such as lower alkyl (e.g. methyl, ethyl, propyl, isopropyl, butyl, isobutyl, pentyl, hexyl, etc.) or the like.

"Aliphatic hydrocarbon group" may include straight or branched alkyl having 1 to 8 carbon atom(s) (e.g. methyl, ethyl, propyl, isopropyl, butyl, isobutyl, t-butyl, pentyl, neopentyl, hexyl, heptyl, octyl, and the like), and more preferably the one having 1 to 4 carbon atom(s), cycloalkyl having 3 to 8 carbon atom(s) (e.g. cyclopropyl, cyclobutyl, cyclopentyl, cyclohexyl, cycloheptyl, cyclooctyl, etc.), or the like, and said aliphatic hydrocarbon group may have suitable substituent(s).

The protective group of the "protected carbonyl group" may include a conventional one of eliminable group and preferably an acetal type protective group such as an acetal with a lower alkylene glycol (e.g. ethylene glycol, trimethylene glycol, ethanedithiol, propanedithiol, etc.), a lower alkanol (e.g. methanol, ethanol, propanol, isopropyl alcohol, etc.), a lower alkanethiol (e.g. methanethiol, ethanethiol, etc.) or the like, or a hydrazone type protective group such as a hydrazone with a carbazate (e.g. methyl carbazate, ethyl carbazate, etc.) or the like.

"Acetal residue which may be linked together" for $A^1$ and $A^2$ may include that $A^1$ and $A^2$ are each lower alkyl (e.g. methyl, ethyl, propyl, isopropyl, butyl, pentyl, hexyl, etc.) or $A^1$ and $A^2$ are linked together to form lower alkylene (e.g. ethylene, trimethylene, etc.), and the like.

"Halogen" may be chlorine, bromine, iodine or fluorine, and preferred one is chlorine or bromine.

More particularly, the preferable examples of the definitions are illustrated as follows.

The preferable examples of $R^1$ may be lower alkyl (e.g. methyl, ethyl, propyl, isopropyl, butyl, pentyl, etc.), and more preferably the one having 1 to 4 carbon atom(s), and the most preferably methyl.

The preferable example of $R^2$ is carboxy.

The preferable examples of $R^3$ may be unsaturated 5 to 6-membered heteromonocyclic group containing 1 to 2 sulfur atom(s) and 1 to 3 nitrogen atom(s) [more preferably, thiadiazolyl (e.g. 1,2,4-thiadiazolyl, 1,3,4-thiadiazolyl, 1,2,5-thiadiazolyl, etc.)] which may have a lower alkyl (e.g. methyl, ethyl, propyl, etc.); or unsaturated condensed heterocyclic group containing 1 to 2 sulfur atom(s) and 1 to 3 nitrogen atom(s) (more preferably, benzothiazolyl).

The preferable examples of $R^4$ and Z may be an esterified carboxy group [more preferably, lower alkoxy carbonyl (e.g. methoxycarbonyl, ethoxycarbonyl, propoxycarbonyl, isopropoxycarbonyl, etc.)].

The preferable examples of $R^5$ may be amino or acylamino, and the most preferably amino.

The preferable examples of $A^1$ and $A^2$ may be each lower alkyl (e.g. methyl, ethyl, propyl, isopropyl, etc.) or $A^1$ and $A^2$ are linked together to form lower alkylene (e.g. ethylene, trimethylene, etc.).

The preferable examples of X may be halogen, and more preferably bromine or chlorine.

The preferable examples of X' and X" may be hydrogen or halogen (more preferably, bromine or chlorine).

The preferable examples of Y may be lower alkylenedioxymethylene (e.g. ethylenedioxymethylene, trimethylenedioxymethylene, etc.), di(lower)alkoxymethylene (e.g. dimethoxymethylene, diethoxymethylene, etc.) or lower alkoxycarbonylhydrazonomethylene (e.g. methoxycarbonylhydrazonomethylene, ethoxycarbonylhydrazonomethylene, etc.).

The preferable examples of Y' may be carbonyl, lower alkylenedioxymethylene (e.g. ethylenedioxymethylene, trimethylenedioxymethylene, etc.), di(-lower)alkoxymethylene (e.g. dimethoxymethylene, diethoxymethylene, etc.) or lower alkoxycarbonylhydrazonomethylene (e.g. methoxycarbonylhydrazonomethylene, ethoxycarbonylhydrazonomethylene, etc.).

"Salt" may be a conventional salt, and may include a salt with an inorganic base or acid, for example, a metal salt such as an alkali metal salt (e.g. sodium salt, potassium salt, etc.) and an alkaline earth metal salt (e.g. calcium salt, magnesium salt, etc.), ammonium salt, an inorganic acid salt (e.g. hydrochloride, hydrobromide, sulfate, phosphate, carbonate, bicarbonate, etc.), a salt with an organic base or acid, for example, an amine salt (e.g. trimethylamine salt, triethylamine salt, pyridine salt, procaine salt, picoline salt, dicyclohexylamine salt, N,N'-dibenzylethylenediamine salt, N-methylglucamine salt, diethanolamine salt, triethanolamine salt, tris(hydroxymethylamino)methane salt, phenethylbenzylamine salt, etc.), an organic carboxylic or sulfonic acid salt (e.g. acetate, maleate, lactate, tartrate, mesylate, benzenesulfonate, tosylate, etc.), a basic or acidic amino acid salt (e.g. arginine salt, aspartic acid salt, glutamic acid salt, lysine salt, serine salt, etc.) and the like, and these salts can suitably be selected according to the kinds of the compounds of the present invention.

The preferable examples of $R^6$ may be hydroxy, acyloxy [more preferably lower alkanoyloxy(e.g. acetoxy, etc.)] or methylene.

Each process of this invention is explained in detail in the following.

Process [A]

The compound (IVa) or (IVb) can be prepared by subjecting the corresponding compound (Va) or (Vb) to acetal-formation reaction.

The present acetal-formation reaction can preferably be carried out by reacting the compound (Va) or (Vb) with an alcohol or an orthoformic acid ester.

Suitable alcohol may include lower alkanol (e.g. methanol, ethanol, propanol, etc.), lower alkylene glycol (e.g. ethylene glycol, propylene glycol, etc.) or the like, and suitable orthoformic acid ester may include orthoformic acid lower alkyl ester (e.g. methyl orthoformate, ethyl orthoformate, etc.).

In case that an alcohol is used in the present reaction, the present reaction can preferably be carried out in the presence of a Lewis acid (e.g. p-toluenesulfonic acid, sulfuric acid, boron trifluoride etherate, amberlist 15 (trademark), etc.) and in a solvent, more preferably in an azeotropic solvent (e.g. benzene, toluene, cyclohexane, 1,2-dichloroethane, 1,2-dichloropropane, etc.) with removal of water produced in the course of the reaction under heating.

In case that an orthoformic acid ester is used in the present reaction, the present reaction can preferably be carried out in the presence of a Lewis acid as aforementioned in a conventional solvent such as a lower alkanol (e.g. methanol, ethanol, etc.) or any other solvent which does not adversely influence the reaction at ambient temperature to under heating.

Process [B]

The compound (IIa) or (IIb) can be prepared by reacting the corresponding compound (IVa) or (IVb) with an alkylating agent capable for introducing a group: -$R^1$ (wherein $R^1$ is as defined above) into the hydroxy group of the compound (IVa) or (IVb).

Suitable alkylating agent may include mono(or di-)-(lower)alkyl sulfate (e.g. mono(or di)-methyl sulfate, mono(or di)ethyl sulfate, etc.), halo(lower)alkane (e.g. iodomethane, etc.), diazo(lower)alkane (e.g. diaziomethane, diazoethane, etc.) or the like.

The present reaction can preferably be carried out in a conventional solvent such as acetone, methyl isobutyl ketone, ethyl acetate or any other solvent which does not adversely influence the reaction.

In case that mono(or di)-(lower)alkyl sulfate or halo(-lower)alkane is used as an alkylating agent in the present reaction, the present reaction can preferably be carried out in the presence of a base (e.g. sodium carbonate, potassium carbonate, etc.).

The reaction temperature is not critical, and the reaction can preferably be carried out under cooling to heating.

Process [C]

The compound (IIa) or (IIb) can be prepared by subjecting the corresponding compound (IIIa) or (IIIb) to acetal-formation reaction.

The present reaction is substantially the same as that of Process [A], and therefore the reaction condition of the present reaction can be referred to that of Process [A].

Process [D]

The compound (IIb) can be prepared by reacting the compound (IIa) with a halogenating agent.

Suitable halogenating agent may include a conventional one which can be used for the halogenation of so-called an activated methylene group, such as halogen (e.g. chlorine, bromine, iodine, etc.), sulfuryl halide (e.g. sulfuryl chloride, sulfuryl bromide, etc.), N-haloimide compound (e.g. N-bromosuccinimide, N-chlorosuccinimide, etc.), a complex of halogen with pyridine (e.g. pyridinium hydrobromide perbromide, etc.), 2-pyrrolidone hydrotribromide, or the like. The present reaction is usually conducted in a solvent such as chloroform, methylene chloride, 1,2-dichoroethane, 1,2-dichloropropane, diethyl ether, diisopropyl ether, tetrahydrofuran, dioxane or any other solvent which does not adversely influence the reaction. The reaction temperature is not critical, and the reaction can preferably be carried out at ambient temperature to under heating.

Process [E]

The compound (Ia) or its salt or (Ib) or its salt can be prepared by hydrolyzing the corresponding compound (IIa) or (IIb).

The present reaction can preferably be carried out in the presence of a base such as an inorganic base (e.g. sodium hydroxide, potassium hydroxide, sodium carbonate, potassium carbonate, sodium acetate, etc.) or an organic base (e.g. trimethylamine, triethylamine, picoline, N-methylmorpholine, etc.) and more preferably in the presence of a strong base, wherein a liquid base can be used as a solvent. The present reaction can preferably be carried out in a solvent such as water, lower alkanol (e.g. methanol, ethanol, etc.) or any other solvent which does not adversely influence the reaction. The reaction temperature is not critical, and the reaction can preferably be carried out under cooling to heating.

Process [F]

The compound (VIII) or its salt can be prepared by reducing the compound (VI) or its salt or (VII) or its salt, and the compound (XII) or its salt can be prepared by reducing the compound (XI) or its salt, respectively.

The reduction may include a conventional one which is applicable for eliminating the acetoxy or heterocyclicthio group to form a methylene group, and preferable method may be reduction using a combination of an acid (e.g. hydrochloric acid, sulfuric acid, formic acid, acetic acid, etc.) and metal (e.g. zinc, iron, copper, etc.), amalgamated metals such as zinc amalgam and aluminum amalgam, bimetallic couples such as the zinc-copper couple, transition metal salt such as chromous choride, chromous bromide, chromous acetate and the like; catalytic reduction using a conventional catalyst (e.g. palladium on carbon, palladium sponge, Raney nickel, platinum, platinum black, etc.) or the like.

The reaction is usually carried out in a conventional solvent such as water, alcohol (e.g. mehanol, ethanol), etc.), N,N-dimethylformamide, tetrahydrofuran or any other solvent which does not adversely influence the reaction. The reaction temperature is not critical, and the reaction can preferably be carried out under cooling to somewhat elevated temperature.

In case that a combination of an acid and a metal is used as a reducing agent, the reaction can advantageously be conducted in the presence of metal sulfate such as copper sulfate and the like.

Process [G]

The compound (IX) or (XIIIa), or a salt thereof can be prepared by oxidizing the corresponding compound (VIII) or (XIIa), or a salt thereof with ozone and subsequently reducing the resultant product.

The reaction of the compound (VIII) or (XIIa), or a salt thereof with ozone can usually be conducted in a solvent which does not adversely influence the reaction, such as water, methanol, ethanol, tetrahydrofuran, methylene chloride, chloroform, diethyl ether, benzene, N,N-dimethylformamide, and the like. Among these solvents, water, methanol, ethanol, tetrahydrofuran or a mixture threof is preferable, since these solvent can also be used in the successive reduction. The reaction temperature is not critical, and the reaction can preferably be carried out within temperature range from cooling to ambient temperature.

The reaction may preferably be carried out in acidic condition (e.g. hydrochloric acid, methanesulfonic acid, etc.).

The method of reduction to be applied in the second step of this process may be a conventional method which is able to reduce the compound obtained above to 3-hydroxy cepham compound, such as reduction using an alkali metal borohydride (e.g. sodium borohydride, etc.), lithium aluminum hydride and the reduction method as mentioned in the Process [F].

Process [H]

The compound (XI) or (XII) or (XIII) or (XIV), or a salt thereof can be prepared by reacting the corresponding compound (VII) or (VIII) or (IX) or (X), or its reactive derivative at the amino group or a salt thereof with a compound of the formula:

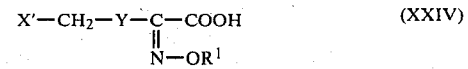

(in which $R^1$, $X'$ and $Y$ are each as defined above) or its reactive derivative at the carboxy group or a salt thereof.

Suitable reactive derivative at the amino group of the compound (VII) or (VIII) or (IX) or (X) may include a conventional reactive derivative as used in a wide variety of amidation reaction, for example, isocyanato, isothiocyanato, a derivative formed by the reaction of a compound (VII) or (VIII) or (IX) or (X) with a silyl compound (e.g. trimethylsilylacetamide, bis(trimethylsilyl)acetamide, etc.), with an aldehyde compound (e.g. acetaldehyde, isopentaldehyde, benzaldehyde, salicylaldehyde, phenylacetaldehyde, p-nitrobenzaldehyde, m-chlorobenzaldehyde, p-chlorobenzaldehyde, hydroxynaphthoaldehyde, furfural, thiophenecarboaldehyde, etc., or the corresponding hydrate, acetal, hemiacetal or enolate thereof), with ketone compound (e.g. acetone, methyl ethyl ketone, methyl isobutyl ketone, acethylacetone, ethyl acetoacetate, etc., or the corresponding ketal, hemiketal or enolate thereof), with phosphorus compound (e.g. phosphorus oxychloride, phosphorus chloride, etc.), or with a sulfur compound (e.g. thionyl chloride, etc.), and the like.

Suitable reactive derivative at the carboxy group of the compound (XXIV) may include, for example, an acid halide, an acid anhydride, an activated amide, an activated ester, and the like, and preferably acid halide such as acid chloride, acid bromide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkylcarbonic acid, aliphatic carboxylic acid (e.g. pivalic acid, pentanoic acid, isopentanoic acid, 2-ethylbutyric acid, trichloroacetic acid, etc.), aromatic carboxylic acid (e.g. benzoic acid, etc.); a summetrical acid anhydride; an activated acid amide with imidazole, 4-substituted imidazole, dimethylpyrazole, triazole or tetrazole; an activated ester (e.g. cyanomethyl ester, methoxymethyl ester, dimethylaminomethyl ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, an ester with a N-hydroxy compound such as N,N-dimethylhydroxylamine, 1-hydroxy-2-(1H)-pyridone, N-hydroxysuccinimide, N-hydroxyphthalimide, 1-hydroxybenzotriazole, 1-hydroxy-6-chlorobenzotriazole, etc.), and the like.

The suitable reactive derivatives of the compounds (VII) or (VIII) or (IX) or (X) can optionally be selected from the above according to the kind of the compounds (VII) or (VIII) or (IX) or (X) to be used practically, and to the reaction conditions.

The reaction is usually carried out in a conventional solvent such as water, acetone, dioxane, acetonitrile, chloroform, benzene, methylene chloride, ethylene chloride, tetrahydrofuran, ethyl acetate, N,N-dimethylformamide, pyridine or any other solvent which does not adversely influence the reaction or an optional mixture thereof.

When the acylating agent (XXIV) is used in a form of free acid or salt in this reaction, the reaction is preferably carried out in the presence of a condensing agent such as a carbodiimide compound (e.g. N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.), a bisimidazolide compound (e.g. N,N'-carbonylbis(2-methylimidazole), etc.), an imine compound (e.g. pentamethyleneketene-N-cyclohexylimine, diphenylketene-N-cyclohexylimine, etc.), an olefinic or acetylenic ether compound (e.g. ethoxyacetylene, β-chlorovinylethyl ether, etc.), 1-(4-chlorobenzenesulfonyloxy)-6-chloro-1H-benzotriazole, N-ethylbenzisoxazolium salt, N-ethyl-5-phenylisoxazolium-3'-sulfonate, a phosphorus compound (e.g. polyphosphoric acid, trialkyl phosphite, ethyl polyphosphate, isopropyl polyphosphate, phosphorus oxychloride, phosphorus trichloride, diethylchlorophosphite, orthophenylene chlorophosphite, etc.), thionyl chloride, oxalyl chloride, Vilsmeier reagent prepared by the reaction of dimethylformamide with thionyl chloride, phosphorus oxychloride, phosgene or the like. The reaction temperature is not critical, and the reaction can preferably be carried out under cooling to warming.

Process [I]

The compound (XIV) or (XVII) or (XIVa), or a salt thereof can be prepared by subjecting the corresponding compound (XIII) or (XVI) or (XIIIa), or a salt thereof, to dehydration reaction.

The dehydration reaction may preferably be conducted by treating a compund (XIII) or (XVI) or (XIIIa), or a salt thereof with a dehydrating agent, which may include an organic sulfonic acid such as an alkane sulfonic acid (e.g. methanesulfonic acid, etc.) or an arenesulfonic acid (e.g. p-toluenesulfonic acid, etc.), an organic carboxylic acid such as a halogenated alkanoic acid (e.g. trifluoroacetic acid, etc.); an organic carboxylic acid anhydride (e.g. acetic anhydride, trifluoroacetic anhydride, etc.); a combination of an acid and acid anhydride (e.g. formic acid and acetic anhydride, etc.); an acid halide such as an organic sulfonic halide (e.g. mesyl chloride, tosyl chloride, etc.), an organic carboxylic acid halide (e.g. acetyl chloride, etc.), an inorganic acid halide (e.g. phosphorus oxychloride, thionyl chloride, etc.) and the like.

The dehydration reaction, especially the reaction using an acid halide or acid anhydride type dehydrating agent may preferably be conducted in the presence of a base. The suitable base may be Lewis base such as an organic base (e.g. trimethylamine, triethylamine, N-methylpiperazine, N,N-dimethylaniline, pyridine, anisole, thioanisole, etc.), an inorganic base (e.g. sodium hydroxide, potassium hydroxide, ammonium hydroxide, sodium carbonate, potassium carbonate, ammonium carbonate sodium acetate, potassium acetate, etc.) and the like.

The reaction can preferably be conducted in an anhydrous conditions and usually carried out in a conventional solvent such as tetrahydrofuran, dioxane, chloroform, methylene chloride, benzene or any solvent which does not adversely influence the reaction.

The reaction temperature is not critical, and the reaction can preferably be carried out at ambient temperature to under heating.

Process [J]

The compound (XV) or (XVI) or (XVII) or (XVIa) or (XVIIb), or a salt thereof can be prepared by subjecting the corresponding compound (XII) or (XIII) or (XIV) or (XIIIa) or (XIVa), or a salt thereof, to elimination reaction of the protective group of the carbonyl.

The elimination reaction can be conducted in a conventional manner, for example, by treating the compound (XII) or (XIII) or (XIV) or (XIIIa) or (XIVa), or a salt thereof with an acid such as a mineral acid (e.g. hydrochloric acid, sulfuric acid, etc.), an inorganic per acid (e.g. perchloric acid, periodic acid, etc.), and the like.

The reaction is carried out in a solvent such as water, methanol, ethanol, acetone, chloroform, methylene chloride, diethyl ether, benzene, dioxane, tetrahydrofuran and the like. The reaction temperature is not critical and the reaction may be carried out under cooling to heating.

Process [K]

The compound (XIIa) or its salt can be prepared by reacting the compound (XVa) or its salt with the compound (XX) or its salt.

The present reaction can preferably be carried out in a conventional solvent such as lower alkanol (e.g. methanol, ethanol, etc.), tetrahydrofuran, benzene or any other solvent which does not adversely influence the reaction.

The present reaction can be carried out in the presence of an acid such as acetic acid, propionic acid or the like. The reaction temperature is not critical and the reaction can preferably be carried out at ambient temperature to under heating.

Process [L]

The compound (XVIIa) or its salt can be prepared by reacting the compound (XVIIb) or its salt with a halogenating agent.

The halogenating agent includes a conventional one which can be used for the halogenation of so-called an activated methylene group, such as halogen (e.g. chlorine, bromine, iodine, etc.), sulfuryl halide (e.g. sulfuryl chloride, etc.), N-haloimide compound (e.g. N-bromosuccinimide, N-chlorosuccinimide, etc.), a complex of halogen with pyridine (e.g. pyridinium hydrobromide perbromide, etc.), 2-pyrrolidone hydrotribromide, or the like. This reaction can preferably be carried out in the presence of a Lewis acid such as aluminium chloride, borontrifluoride, titanium tetrachloride and the like.

The reaction can preferably be conducted in an inert solvent such as tetrahydrofuran, dioxane, chloroform, methylene chloride, benzene and the like.

The reaction temperature is not critical and the reaction may be carried out under cooling to heating.

Process [M]

The compound (XIX) or its salt can be prepared by reacting the compound (XVIIa) or its salt with the compound (XVIII).

Suitable examples of the compound (XVIII) may be thiourea, N-substituted or unsubstituted lower alkanoyl)thiourea (e.g. N-formylthiourea, N-acetylthiourea, N-trifluoroacetylthiourea, etc.), N-(substituted or unsubstituted lower alkoxy carbonyl)thiourea (e.g. N-trichloroethoxycarbonyl thiourea, etc.), or the like.

The reaction is usually conducted in a solvent such as water, alcohol (e.g. methanol, ethanol, etc.), benzene, N,N-dimethylformamide, tetrahydrofuran or any other solvent which does not adversely influence the reaction. The reaction temperature is not critical, and the reaction can preferably be carried out at ambient temperature to under heating. The present reaction can preferably be carried out in the presence of a base as aforementioned in Process [E].

In order to show the utility of the active compound (XIX), the test data of the representative compound (XI), i.e. 7-[2-(2-aminothiazol-4-yl)-2-methoxyiminoacetamido]-3-cephem-4-carboxylic acid (syn isomer) are shown in the following.

1. In vitro antibacterial activity (1) Test method

In vitro antibacterial activity was determined by the two-fold agar-plate dilution method as described below.

One loopful of the 100-fold dilution of an overnight culture of each test strain in Trypticase-soy broth was streaked on heart infusion agar (HI-agar) containing graded concentrations of the test compound and incubated at 37° C. for 20 hours. The minimal inhibitory concentration (MIC) was expressed in μg/ml.

(2) Test results:

| Compound No.<br>Test Strains | MIC (μg/ml)<br>1 |
|---|---|
| Staphylococcus aureus 209P JC-1 | 6.25 |
| Escherichia coli. NIHJ JC-2 | $\leq 0.025$ |
| Proteus vulgaris IAM-1025 | $\leq 0.025$ |
| Klebsiella pneumoniae 20 | $\leq 0.025$ |
| Proteus mirabilis 18 | $\leq 0.025$ |
| Pseudomonus aeruginosa NCTC-10490 | 0.39 |
| Serratia marcescens 35 | 1.56 |

2. Protecting effect against experimental infections in mice (1) Test method Male ICR strain mice aged 4 weeks, each weighing 18.5–21.5 g. were used in groups of 10 mice. The test bacteria were cultured overnight at 37° C. on Trypticase-soy agar and then suspended in 5% mucin to obtain the suspension corresponding to each challenge cells. Mice were inoculated intraperitoneally with 0.5 ml. of the suspension. A solution of test compound was given subcutaneously to the mice in various dosage one hour after the challenge. The $ED_{50}$ values were calculated from the number of surviving mice for each dosage after four days of observation.

(2) Test results

| Test Bacteria | Inoculated Cells/mouse | $ED_{50}$ (s.c.) (mg/kg) Test compound | Ref-[*4]erence | MIC (μg/ml) Inoculum size | Test compound | Reference |
|---|---|---|---|---|---|---|
| Escherichia coli 54 | $1.1 \times 10^7$ | 0.95 | 2.8 | $10^{0*1}$<br>$10^{-2*2}$ | 0.78<br>0.05 | 3.13<br>0.1 |
| Klebsiella pneumoniae 39 | $8 \times 10^6$ | <0.98 | 0.995 | $10^0$<br>$10^{-2}$ | 0.39<br>$\leq 0.025$ | 3.13<br>0.05 |
| Proteus rettgeri 24 | $9.9 \times 10^6$ | 0.39 | 1.171 | $10^0$<br>$10^{-2}$ | 1.56<br>$\leq 0.025$ | 50<br>0.1 |
| Serratia Marcescens 58 | $1.2 \times 10^7$ | 3.562[*3] | 31.427[*3] | $10^0$<br>$10^{-2}$ | 25<br>0.39 | 50<br>1.56 |

[*1] overnight culture
[*2] 100-fold dilution of the overnight culture
[*3] treated with two divisional doses at 1 hr. and 3 hrs. after infection
[*4] 7-[2-(2-Amino-4-thiazolyl)-2-methoxyiminoacetamido] cephalosporanic acid (syn isomer)

3. Acute toxicity (1) Test method

Ten male and 10 female rats aged 6 weeks (ICL-SD strain) were used per group. Test compound dissolved in distilled water was given subcutaneously and intravenously to the animals. These animals were observed for 7 days after dosing. The $LD_{50}$ values were calculated from the number of dead animals by the Litchfield-Wilcoxon method.

(2) Test results

| Test animal | Sex | $LD_{50}$ (mg/kg) s.c. | i.v. |
|---|---|---|---|
| Rat | Male | >8000 | about 8000 |
| | Female | >8000 | >8000 |

Process [I] (Supplemenetal explanations of Process [I] as aforementioned.)

When an acylating agent is used as a dehydrating agent in this process, the starting compound (XIII) or (XVI) or (XIIIa) may be often acylated in the course of the reaction and produce the corresponding 3-acyloxycepham compound as an intermediate which can be also led to the compound (XIV) or (XVII) or (XIVa) by treating the said 3-acyloxycepham compound with or without isolating, with a base as aforementioned.

The following examples are given only for explaining this invention in more detail.

EXAMPLE 1

Preparation of 2-methoxyimino-3,3-ethylenedioxybutyric acid (syn isomer)

(1) To a solution of ethyl 2-methoxyimino-3-oxobutyrate (syn isomer, 200 g) in ethylene glycol (179 g) were added dried benzene (3 l) and p-toluenesulfonic acid (6 g), and the mixture was heated for 20 hours under reflux while removing water azeotropically. The reaction mixture was cooled to ambient temperature, washed with water, a saturated aqueous solution of sodium bicarbonade, water and a saturated aqueous solution of sodium chloride in turn, dried over magnesium sulfate and then filtered. After the filtrate was evaporated, the residual oil was distilled under reduced pressure to give ethyl 2-methoxyimino-3,3-ethylenedioxybutyrate (syn isomer), bp 89.5°–91° C./0.6 mmHg, in 85.5% yield.

(2) To a solution of ethyl 2-methoxyimino-3,3-ethylenedioxybutyrate (syn isomer, 180 g) in ethanol (1080 ml) was added 1 N aqueous solution of sodium hydroxide (1660 ml) and the mixture was stirred for 2 hours and 10 minutes at ambient temperature. After the reaction mixture was adjusted to pH 7.3 with 6 N hydrochloric acid, ethanol was distilled off under reduced pressure and then washed with diethyl ether (500 ml×2). To the resultant was added diethyl ether (1 l), adjusted to pH 1.5 with 6 N hydrochloric acid and then diethyl ether layer was separated. The remaining aqueous layer was further extracted with diethyl ether (350 ml), and the remaining aqueous layer was adjusted to pH 1.3 with 6 N hydrochloric acid and then further extracted with diethyl ether (350 ml×2). The diethyl ether layer and extracts were combined together, washed with a saturated aqueous solution of sodium chloride, dried over magnesium sulfate and then filtered. The filtrate was concentrated to give an oil (155.6 g) of 2-methoxyimino-3,3-ethylenedioxybutyric acid (syn isomer). (Yield: 99.3%)

I.R. (Nujol): 3700-2200, 1740, 1640, 1470, 1450, 1400, 1380, 1260, 1240, 1210, 1150, 1130, 1080, 1030, 1055, 870, 820 cm$^{-1}$ N.M.R. $\delta$(DMSO-d$_6$, ppm): 1.55 (3H, s), 3.85 (3H, s), 3.97 (4H, s)

EXAMPLE 2

Preparation of 2-methoxyimino-3,3-ethylenedioxybutyric acid (syn isomer)

(1) A solution of ethyl 2-methoxyimino-3-oxobutyrate (syn isomer 17.3 g), ethylene glycol (12.4 g) and p-toluenesulfonic acid (0.5 g) in benzene (260 ml) was heated under reflux while removing water. The resultant solution was washed with a saturated aqueous solution of sodium bicarbonate and a saturated aqueous solution of sodium chloride in turn and dried over magnesium sulfate.

After evaporating the solvent from the solution, the residue was distilled under reduced pressure to give ethyl 2-methoxyimino-3,3-ethylenedioxybutyrate (syn isomer, 15.2 g), bp 97° to 102° C./4 mmHg.

N.M.R. $\delta$(CDCl$_3$, ppm): 1.34 (3H, t, J=7 Hz), 1.64 (3H, s), 3.92 (3H, s), 4.02 (4H, s), 4.33 (2H, q, J=7 Hz)

(2) 1 N Aqueous sodium hydroxide (130 ml) was added to a solution of ethyl 2-methoxyimino-3,3-ethylenedioxybutyrate (syn isomer, 25.7 g) in ethanol (150 ml), and stirred at ambient temperature overnight. The resultant solution was concentrated under reduced pressure. The residue was dissolved in a saturated aqueous solution of sodium chloride (80 ml) and washed with diethyl ether. Diethyl ether (100 ml) was added to the aqueous solution, adjusted to pH 1 with 10% hydrochloric acid and the diethyl ether layer was separated. The aqueous layer was extracted with diethyl ether (50 ml) twice. The diethyl ether layer and the extracts were combined, washed with a saturated aqueous solution of sodium chloride and dried over magnesium sulfate. After evaporating the solvent, the residue was crystallized and washed with n-hexane. The precipitates were collected by filtration and dried to give 2-methoxyimino-3,3-ethylenedioxybutyric acid (syn isomer, 17.7 g).

I.R. (Nujol): 2650-2200, 1735, 1630 cm$^{-1}$

N.M.R. $\delta$(CDCl$_3$, ppm): 1.66 (3H, s), 3.94 (3H, s), 4.05 (4H, s)

EXAMPLE 3

Preparation of 2-methoxyimino-3,3-ethylenedioxy-4-chlorobutyric acid (syn isomer)

(1) A mixture of ethyl 2-methoxyimino-3-oxo-4-chlorobutyrate (syn isomer, 41 g), ethylene glycol (24.6 g), p-toluenesulfonic acid (2.0 g) and toluene (250 ml) was heated for 20 hours under reflux while removing water. The reaction mixture was cooled to ambient temperature, washed with a saturated aqueous solution of sodium bicarbonate, a saturated aqueous solution of sodium chloride in turn, dried over magnesium sulfate and then the solvents were removed. The residue was distilled under reduced pressure to give ethyl 2-methoxyimino-3,3-ethylenedioxy-4-chlorobutyrate (syn isomer, 24.4 g), bp 103°–110° C./2 mmHg.

I.R. (film): 1735, 1625, 1600 cm$^{-1}$

N.M.R. $\delta$(CDCl$_3$, ppm): 1.37 (3H, t, J=7 Hz), 3.92 (2H, s), 3.97 (3H, s), 4.17 (4H, s), 4.37 (2H, q, J=7 Hz)

(2) To a solution of ethyl 2-methoxyimino-3,3-ethylenedioxy-4-chlorobutyrate (syn isomer, 7.3 g) in ethanol (35 ml) was added 1 N aqueous solution of sodium hyroxide (35 ml) and the mixture was stirred for 2 hours at 40°–45° C. and then evaporated under reduced pressure. To the residue was added a saturated aqueous solution of sodium chloride (50 ml) and the mixture was washed with diethyl ether (60 ml). The aqueous layer was separated and then diethyl ether (100 ml) was added thereto. The mixture was adjusted to pH 1 with 10% hydrochloric acid, and the diethyl ether layer was separated and then the remaining aqueous layer was further extracted with diethyl ether (50 ml×2). The diethyl ether layer and extracts were combined together, washed with a saturated aqueous solution of sodium chloride, dried over magnesium sulfate and then the solvent was distilled off.

To the resultant oil was added benzene, and the benzene was distilled off. The resultant solid was washed in ligroin, collected by filtration and then dried to give 2-methoxyimino-3,3-ethylenedioxy-4-chlorobutyric acid (syn isomer, 5.4 g), mp 80°–81° C. (Yield: 83.3%).

I.R. (Nujol): 2500-2200, 1720, 1655, 1625 cm$^{-1}$

N.M.R. $\delta$(CDCl$_3$, ppm): 3.92 (2H, s), 4.02 (3H, s) 4.20 (4H, s)

EXAMPLE 4

Preparation of 2-methoxyimino-3,3-ethylenedioxy-4-chlorobutyric acid (syn isomer)

(1) To a solution of ethyl 2-methoxyimino-3,3-ethylenedioxybutyrate (syn isomer, 30 g) in acetic acid (150 ml) was added lithium chloride (7 g) and the mixture was stirred for 15 minutes at ambient temperature.

To the mixture was added dropwise sulfuryl chloride (22.4 g), and the mixture was stirred for one hour at ambient temperature and then allowed to stand for overnight. To the reaction mixture was added water (600 ml) under ice-cooling and stirring, and diisopropyl ether (400 ml) was added thereto and then stirred. The diisopropyl ether layer was separated, and the remaining aqueous layer was further extracted with diisopropyl ether. The diisopropyl ether layer and extract were combined together, washed with water, a saturated aqueous solution of sodium bicarbonate, water and a saturated aqueous solution of sodium chloride in turn, dried over magnesium sulfate and then filtered. The filtrate was concentrated and the residual oil (31.2 g) was distilled under reduced pressure to give ethyl 2-methoxyimino-3,3-ethylenedioxy-4-chlorobutyrate (syn isomer), bp 104°–106° C./0.32–0.35 mmHg.

I.R. (Nujol): 2970, 2930, 2900, 2820, 1730, 1620, 1460, 1445, 1420, 1375, 1300, 1280, 1260, 1210, 1200, 1140, 1040 cm$^{-1}$ N.M.R. $\delta$(CDCl$_3$, ppm): 1.33 (3H, t, J=7 Hz), 3.90 (2H, s), 3.97 (3H, s), 4.17 (4H, s), 4.34 (2H, q, J=7 Hz)

(2) To a solution of ethyl 2-methoxyimino-3,3-ethylenedioxy-4-chlorobutyrate (syn isomer, 10.4 g) in ethanol (30 ml) was added an aqueous solution (10 ml) of sodium hydroxide (3.3 g) under ice-cooling, and the mixture was stirred for 30 minutes at ambient temperature. The reaction mixture was adjusted to pH 7 with 20% sulfuric acid under ice-cooling and stirring, and water (30 ml) was added thereto, and then the solvents are distilled off. To the residue was added water (30 ml), and the resultant solution was washed with diisopropyl ether (50 ml). To the aqueous solution was added diisopropyl ether (100 ml), adjusted to pH 2 with 20% sulfuric acid under ice-cooling and stirring and then saturated with sodium chloride. The diisopropyl ether layer was separated, and the remaining aqueous layer was further extracted with diisopropyl ether. The diisopropyl ether layer and extracts were combined together, washed with a saturated aqueous solution of sodium chloride, dried over magnesium sulfate, treated with an activated carbon and then filtered. The filtrate was concentrated and the remaining oil was allowed to stand for 1 hour under reduced pressure to give crystals of 2-methoxyimino-3,3-ethylenedioxy-4-chlorobutyric acid (syn isomer), mp 80°–81° C. in yield of 99.6%.

I.R. (Nujol): 2650, 2500, 1720, 1655, 1620, 1465, 1430, 1400, 1300, 1255, 1215, 1050, 1020 cm$^{-1}$ N.M.R. $\delta$(DMSO-d$_6$, ppm): 3.80 (2H, s), 3.83 (3H, s), 4.00 (4H, d)

EXAMPLE 5

Preparation of 2-methoxyimino-3,3-ethylenedioxy-4-bromobutyric acid (syn isomer)

(1) A solution of bromine (14.72 g) in chloroform (30 ml) was added to a stirred solution of ethyl 2-methoxyimino-3,3-ethylenedioxybutyrate (syn isomer, 20 g) in chloroform (200 ml) at ambient temperature and stirred at the same temperature for an hour. To the resultant solution was added 5% sodium thiosulfate aqueous solution (100 ml) and stirred at ambient temperature for 10 minutes. The organic layer was separated, washed with 5% sodium thiosulfate aqueous solution (100 ml), water (100 ml), a sodium bicarbonate saturated aqueous solution and sodium chloride saturated solution in turn and then dried over magnesium sulfate. The solution was evaporated in vacuo and the remaining oil (33.4 g) was distilled under reduced pressure to give an oil of ethyl 2-methoxyimino-3,3-ethylenedioxy-4-bromobutyrate (syn isomer), bp 0.95 mm/Hg 115°–118° C. (Yield: quantitative).

I.R. (film): 3000, 2960, 1745, 1630, 1300, 1265, 1200, 1040 cm$^{-1}$

N.M.R. $\delta$(DMSO-d$_6$, ppm): 1.33 (3H, t, J=6 Hz), 3.78 (2H, s), 3.93 (3H, s), 4.17 (4H, s), 4.35 (2H, q, J=6 Hz)

(2) A solution of sodium hydroxide (8.64 g) in water (20 ml) was added to a solution of ethyl 2-methoxyimino-3,3-ethylenedioxy-4-bromobutyrate (syn isomer, 26.6 g) in methanol (60 ml) under ice-cooling, stirred at ambient temperature for 2 hours. Water (100 ml) was added to the resultant solution and adjusted to pH 7.0 with 20% sulfuric acid under ice-cooling. After removing methanol therefrom in vacuo, the solution was washed with diethyl ether (100 ml). Diethyl ether (100 ml) was added to the aqueous layer and adjusted to pH 2.0 with 20% sulfuric acid below 10° C. The organic layer was separated, and then the aqueous layer was extracted with diethyl ether (100 ml) twice. The organic layer was washed with water and a sodium chloride saturated aqueous solution in turn, and dried over magnesium sulfate. The solution was concentrated in vacuo and the residue was allowed to stand in refrigerator overnight to give 2-methoxyimino-3,3-ethylenedioxy-4-bromobutyric acid (syn isomer, 18.0 g). (Yield: 74.7%).

I.R. (Nujol): 2600, 1755, 1650, 1290, 1230, 1170, 1060, 1035, 1015 cm$^{-1}$

N.M.R. $\delta$(DMSO-d$_6$, ppm): 3.73 (2H, s), 3.8 (3H, s), 4.03 (4H, d, J=2 Hz)

EXAMPLE 6

Preparation of ethyl 2-methoxyimino-3,3-ethylenedioxybutyrate (syn isomer)

(1) A mixture of ethyl 2-hydroxyimino-3-oxobutyrate (syn isomer, 10 g), ethylene glycol (19.75 g) and p-toluenesulfonic acid (0.3 g) and dried benzene (150 ml) was heated for 2 hours under reflux while removing water azeotropically. The reaction mixture was washed with water (50 ml), a saturated aqueous solution of sodium bicarbonate (50 ml), water (50 ml) and a saturated aqueous solution of sodium chloride (50 ml) in turn, dried over magnesium sulfate and then filtered. The filtrate was evaporated to give an oil of ethyl 2-hydroxyimino-3,3-ethylenedioxybutyrate (syn isomer, 7.12 g). (Yield: 55.1%).

I.R. (film): 3350, 2960, 2880, 1730, 1370, 1280, 1200, 1060, 1030, 960, 945, 880 cm$^{-1}$ N.M.R. $\delta$(CCl$_4$, ppm): 1.33 (3H, t, J=7 Hz), 1.58 (3H, s), 3.97 (4H, s), 4.33 (2H, q, J=7 Hz), 9.67 (1H, s, broad)

(2) To a solution of ethyl 2-hydroxyimino-3,3-ethylenedioxybutyrate (syn isomer, 5 g) in dried ethyl acetate (20 ml) was added potassium carbonate (5.78 g), and dimethyl sulfate (3.96 ml) was added dropwise thereto at ambient temperature with stirring, and then the mixture was stirred for 2 hours at 43°–45° C. To the reaction mixture were added water (10 ml) and ethyl acetate (5 ml), and the mixture was stirred for 40 minutes at ambient temperature. The mixture was adjusted to pH 7.2 with 6 N hydrochloric acid and saturated with sodium chloride, and then ethyl acetate layer was separated. The remaining aqueous layer was further extracted with ethyl acetate (10 ml). The ethyl acetate layer and extract were combined together, washed with a saturated aqueous solution of sodium chloride, dried over magnesium sulfate and then filtered. The filtrate was evaporated to give ethyl 2-methoxyimino-3,3-ethylenedioxybutyrate (syn isomer), quantitatively.

I.R. (film): 2990, 2950, 2900, 1740, 1620, 1470, 1450, 1380, 1285, 1220, 1080, 1040 cm$^{-1}$ N.M.R. δ(CDCl$_3$, ppm): 1.33 (3H, t, J=7 Hz), 1.67 (3H, s), 3.93 (3H, s), 4.03 (4H, s), 4.33 (2H, q, J=7 Hz)

Thus obtained product can be led to 2-methoxyimino-3,3-ethylenedioxybutyric acid (syn isomer) or 2-methoxyimino-3,3-ethylenedioxy-4-chlorobutyric acid (syn isomer) or 2-methoxyimino-3,3-ethylenedioxy-4-bromobutyric acid (syn isomer) according to the manner described in Examples 1 or 2 or 3 or 4 or 5.

EXAMPLE 7

Preparation of ethyl 2-methoxyimino-3,3-ethylenedioxy-4-chlorobutyrate (syn isomer)

(1) To a solution of ethyl 2-hydroxyimino-3-oxobutyrate (syn isomer, 31.83 g) in chloroform (70 ml) was added dropwise sulfuryl chloride (29.7 g) over 6 minutes under ice-cooling, and the mixture was stirred for 4.5 hours at ambient temperature. The mixture was cooled to 7° C., and sulfuryl chloride (13.498 g) was further added thereto. The mixture was stirred at ambient temperature for overnight. After the reaction mixture was cooled with ice-water, chloroform (50 ml) and water (40 ml) were added thereto with stirring. The mixture was saturated with sodium chloride, and the organic layer was separated, washed with a saturated aqueous solution of sodium chloride (40 ml×2), dried over magnesium sulfate and then filtered. The filtrate was evaporated to give ethyl 2-hydroxyimino-3-oxo-4-chlorobutyrate (syn isomer), quantitatively.

I.R. (film): 3700-3100, 2980, 2875, 1720, 1630, 1480, 1455, 1400, 1380, 1335, 1280, 1200, 1100, 1030, 980 cm$^{-1}$ N.M.R. δ(CCl$_4$, ppm): 1.37 (3H, t, J=7 Hz), 4.37 (2H, q, J=7 Hz), 4.52 (2H, s), 10.65 (1H, s)

(2) A mixture of ethyl 2-hydroxyimino-3-oxo-4-chlorobutyrate (syn isomer, 10 g), ethylene glycol (16 g), p-toluenesulfonic acid (0.3 g) and dried benzene (100 ml) was heated for 19 hours under reflux while removing water azeotropically. After the reaction mixture was cooled to ambient temperature, water (30 ml) and benzene (20 ml) were added thereto. The mixture was saturated with sodium chloride and the benzene layer was separated, and the remaining aqueous layer was further extracted with benzene (20 ml). The benzene layer and extract were combined together, washed with a saturated aqueous solution of sodium chloride (30 ml×2), dried over magnesium sulfate and then filtered. The filtrate was evaporated to give an oil of ethyl 2-hydroxyimino-3,3-ethylenedioxy-4-chlorobutyrate (syn isomer, 7.23 g). (Yield: 58.9%).

I.R. (film): 3675-3125, 2980, 2910, 1730, 1455, 1430, 1380, 1290, 1190, 1095, 1030, 955 cm$^{-1}$ N.M.R. δ(CCl$_4$, ppm): 1.33 (3H, t, J=7 Hz), 3.77 (2H, s), 4.05 (4H, s), 4.28 (2H, q, J=7 Hz), 9.67 (1H, s)

(3) To a solution of ethyl 2-hydroxyimino-3,3-ethylenedioxy-4-chlorobutyrate (syn isomer, 0.5 g) in dried acetone (5 ml) was added potassium carbonate (0.29 g), and then dimethyl sulfate (0.265 g) was added dropwise thereto at ambient temperature with stirring. The mixture was stirred for 7 hours at ambient temperature and then filtered. The filtrate was evaporated to give ethyl 2-methoxyimino-3,3-ethylenedioxy-4-chlorobutyrate (syn isomer).

I.R. (film): 2970, 2930, 2900, 2820, 1730, 1620, 1460, 1445, 1420, 1375, 1300, 1280, 1260 (sh), 1210, 1200, 1140, 1040 cm$^{-1}$ N.M.R. δ(CDCl$_3$, ppm): 1.33 (3H, t, J=7 Hz), 3.90 (2H, s), 3.97 (3H, s), 4.17 (4H, s), 4.34 (2H, q, J=7 Hz)

Thus obtained product can be led to 2-methoxyimino-3,3-ethylenedioxy-4-chlorobutyric acid (syn isomer) according to the manner described in Example 3(2) or 4(2).

EXAMPLE 8

Preparation of 2-methoxyimino-3,3-dimethoxy-4-bromobutyric acid (syn isomer)

(1) Methyl orthoformate (31.8 g) and "Amberlist 15" (trademark) (1.7 g) were added to a stirred solution of ethyl 2-methoxyimino-3-oxobutyrate (syn isomer, 17.3 g) in dry methanol (50 ml) and stirred at 50° to 60° C. for 2.5 hours. To the resultant solution was added methyl orthoformate (10.6 g) and stirred for 2 hours. The solution was allowed to stand in refrigerator overnight and stirred at 50° to 60° C. for 2 hours. After evaporating methanol in vacuo, diethyl ether (100 ml) and water (50 ml) were added to the residue, and the organic layer was separated. The aqueous layer was extracted with diethyl ether. The organic layer and the extract were combined together and washed with a saturated aqueous solution of sodium chloride. The solution was dried over magnesium sulfate and evaporated under reduced pressure to give ethyl 2-methoxyimino-3,3-dimethoxybutyrate (syn isomer, 18 g). bp 61° to 64° C./0.35 mmHg.

I.R. (film): 3000, 2950, 2920, 2850, 1750, 1640, 1480, 1460, 1400, 1380, 1310, 1250, 1205, 1195, 1160, 1120, 1085, 1060, 1040, 890 cm$^{-1}$ N.M.R. δ(CCl$_4$, ppm) 1.28 (3H, t, J=7 Hz), 1.47 (3H, s), 3.17 (6H, s), 3.85 (3H, s), 4.18 (2H, q, J=7 Hz)

(2) Pyridinium hydrobromide perbromide (1.82 g) was added to a solution of ethyl 2-methoxyimino-3,3-dimethoxybutyrate (syn isomer, 1.0 g) in dry tetrahydrofuran (10 ml) and heated under reflux for an hour. The resultant solution was poured into water (30 ml) and extracted with diethyl ether (10 ml×2). The extract was washed with 5% aqueous sodium thiosulfate solution (5 ml×5) and a saturated aqueous solution of sodium chloride (10 ml×1) successively. The solution was dried over magnesium sulfate and evaporated under reduced pressure to give ethyl-2-methoxyimino-3,3-dimethoxy-4-bromobutyrate (syn isomer, 2.02 g).

I.R. (film): 3700-2500, 1730, 1620, 1600, 1460, 1440, 1385, 1365, 1305, 1245, 1200, 1150, 1100, 1060, 1030 cm$^{-1}$ N.M.R. δ(CDCl$_3$, ppm): 1.33 (3H, t, J=7 Hz), 3.33 (6H, s), 3.83 (2H, s), 3.97 (3H, s), 4.32 (2H, q, J=7 Hz)

(3) 2 N Methanolic solution (6.5 ml) of sodium hydroxide was added to a solution of ethyl 2-methoxyimino-3,3-dimethoxy-4-bromobutyrate (1.06 g) in methanol (1 ml) under ice-cooling and stirred at room temperature for 3 hours. To the resultant solution were added diethyl ether (20 ml) and water (20 ml). The organic layer was separated.

To the aqueous layer was added diethyl ether (30 ml) and the solution was adjusted to pH 1.6 with 6 N hydrochloric acid below 10° C. The organic layer was separated and the aqueous layer was extracted with diethyl ether (30 ml). The organic layer and the extract were combined together, washed with water and a saturated aqueous solution of sodium chloride successively and dried over magnesium sulfate.

The solution was evaporated under reduced pressure to give 2-methoxyimino-3,3-dimethoxy-4-bromobutyric acid (syn isomer), 0.4 g), oil.

I.R. (film): 3700-2700, 2700-2200, 1740, 1640, 1480, 1475, 1455, 1430, 1400, 1310, 1260, 1220, 1160, 1120, 1060, 1040, 970, 890, 835 cm$^{-1}$ N.M.R. $\delta$(CDCl$_3$, ppm): 3.33 (3H, s), 3.50 (3H, s), 3.70 (2H, s), 4.00 (3H, s)

EXAMPLE 9

Preparation of 2-methoxyimino-3,3-diethoxy-4-bromobutyric acid (syn isomer)

(1) Ethyl orthoformate (1.71 g), "Amberlist 15" (trademark) (200 mg) and ethyl 2-methoxyimino-3-oxobutyrate (syn isomer, 0.5 g) in dry ethanol (2 ml) were treated in a similar manner to that of Example 8 (1) to give ethyl 2-methoxyimino-3,3-diethoxybutyrate (syn isomer, 0.35 g).

I.R. (film): 2980, 2950, 2900, 1750, 1640, 1600, 1500, 1480, 1460, 1400, 1380, 1310, 1250, 1180, 1130, 1100, 1080, 1060, 1040 cm$^{-1}$ N.M.R. $\delta$(CCl$_4$, ppm): 1.13 (6H, t, J=7 Hz), 1.28 (3H, t, J=7 Hz), 1.50 (3H, s), 3.50 (4H, q, J=7 Hz), 3.85 (3H, s), 4.18 (2H, q, J=7 Hz)

(2) Ethyl 2-methoxyimino-3,3-diethoxybutyrate (syn isomer, 10.0 g), pyridinium hydrobromide perbromide (15.5 g) and tetrahydrofuran (100 ml) were treated in a similar manner to that of Example 8 (2) to give ethyl 2-methoxyimino-3,3-diethoxy-4-bromobutyrate (syn isomer, 16.20 g).

I. R. (film): 3000-2900, 1730, 1620, 1600, 1440, 1390, 1360, 1300, 1250, 1190, 1150, 1110, 1090, 1040 cm$^{-1}$ N.M.R. $\delta$(CCl$_4$, ppm): 1.10-1.42 (9H, m), 3.42 (4H, q, J=6.0 Hz), 3.60 (2H, s), 3.92 (3H, s), 4.22 (2H, q, J=6.0 Hz)

(3) Ethyl 2-methoxyimino-3,3-diethoxy-4-bromobutyrate (syn isomer, 10.0 g), a solution of sodium hydroxide (3.68 g) in water (70 ml) and ethanol (100 ml) were treated in a similar manner to that of Example 8 (3) to give 2-methoxyimino-3,3-diethoxy-4-bromobutyric acid (syn isomer, 4.97 g).

I. R. (film): 3450, 3000-2900, 2600, 1730, 1620, 1440, 1420, 1390, 1290, 1240, 1190, 1150, 1110, 1090, 1040 cm$^{-1}$ N.M.R. $\delta$(CDCl$_3$, ppm): 1.17 (3H, t, J=6 Hz), 1.25 (3H, t, J=6 Hz), 3.49 (4H, q, J=6 Hz), 3.66 (2H, s), 3.91 (3H, s), 7.00 (1H, s).

EXAMPLE 10

(1) To a mixture of 7-aminocephalosporanic acid (23.1 g., purity 86.4%) and 2-mercaptobenzothiazole (14.7 g.) in water (800 ml.), sodium bicarbonate (13.5 g.) was added portionwise with stirring, and acetone (250 ml.) was added thereto. The mixture was stirred at 73° C. for 4.5 hours, cooled below 20° C. and adjusted to pH 3.4 with 6 N hydrochloric acid. The precipitating crystals were collected by filtration, washed with water and acetone in turn and dried under reduced pressure to give 7-amino-3-(benzothiazol-2-yl)thiomethyl-3-cephem-4-carboxylic acid (18.7 g.).

I.R. $\nu_{max}^{Nujol}$: 3800-2800, 1800, 1620, 1540, 1425, 1410 (sh), 1350, 1020 (sh), 1010, 1000, 820, 800, 785, 755, 730 cm$^{-1}$ N.M.R. $\delta$(D$_2$O+NaHCO$_3$, ppm): 3.22, 3.62 (2H, d,d, J=15 Hz), 4.06, 4.4 (2H, d,d, J=13 Hz), 5.02 (1H, d, J=5 Hz), 5.55 (1H, d, J=5 Hz), 7.0-7.88 (4H, m)

(2) Trimethylsilylacetamide (6.57 g.) was added to a suspension of 7-amino-3-(benzothiazol-2-yl)-thiomethyl-3-cephem-4-carboxylic acid (3.8 g.) in ethyl acetate (80 ml.), and stirred at room temperature for an hour. On the other hand, thionyl chloride (1.5 g.) was added to a stirred solution of N,N-dimethylformamide (0.92 g.) in ethyl acetate (10 ml.), and stirred under ice-cooling for 30 minutes. To the solution was added 2-methoxyimino-3,3-ethylenedioxybutyric acid (syn isomer, 2.27 g.) and stirred at 5° to 10° C. for 2 hours. Thus obtained activated acid solution was added to the above solution at −30° C. over 45 minutes, and stirred at the same temperature for 2 hours. The resultant mixture was diluted with water (100 ml.) and stirred for 10 minutes. After removing the insoluble substance from the resultant mixture by filtration, the fitrate was extracted with a mixture solvent (200 ml.) of ethyl acetate and methanol (4:1) twice. The insoluble substance obtained above was suspended in the mixed solvent (200 ml.) of ethyl acetate and methanol (4:1), stirred for 30 minutes, and filtered. The filtrate and the above extract were combined, washed with saturated aqueous sodium chloride, dried over magnesium sulfate and concentrated in vacuo. Diisopropyl ether was added to the residue and allowed to stand in a refrigerator. After removing the solvent by decantation, the residue was triturated with n-hexane to give 7-[2-methoxyimino-3,3-ethylenedioxybutyramido]-3-(benzothiazol-2-yl)thiomethyl-3-cephem-4-carboxylic acid (syn isomer, 3.7 g.).

I.R. $\nu_{max}^{Nujol}$: 3700-2000, 1780, 1720, 1685 (sh), 1670, 1620 (sh), 1520, 1430, 1240, 1200, 1165 (sh), 1100, 1080, 1040, 1000 cm$^{-1}$ N.M.R. $\delta$(DMSO-d$_6$, ppm): 1.50 (3H, s), 3.3–4.0 (2H, broad s), 3.8 (3H, s), 3.93 (4H, s), 4.23, 4.83 (2H, d,d, J=12 Hz), 5.1 (1H, d, J=5 Hz), 5.71 (1H, d,d, J=5 Hz, 8 Hz), 7.27–7.67 (2H, m), 7.67–8.17 (2H, m), 9.37 (1H, d, J=8 Hz)

(3) Method A

Formic acid (10 ml.), tetrahydrofuran (40 ml.) and water (10 ml.) were added to a solution of 7-[2-methoxyimino-3,3-ethylenedioxybutyramido]-3-(benzothiazol-2-yl)thiomethyl-3-cephem-4-carboxylic acid (syn isomer, 2 g.) in N,N-dimethylformamide (10 ml.). Zinc powder (1.4 g.) was added to the stirred mixture at 0° to 2° C., and stirred at the same temperature for 1.5 hours. The reaction mixture was filtered, and the residue was washed with tetrahydrofuran. The filtrate and the washings were combined and concentrated in vacuo. The residue was diluted with water (50 ml.) and extracted with ethyl acetate (150 ml.). The extract was washed with water and extracted with an aqueous solution of sodium bicarbonate. Ethyl acetate (50 ml.) was added to the extract and acidified to pH 2.0 with 6 N hydrochloric acid. After the organic layer was separated, the aqueous layer was extracted with ethyl acetate (50 ml.). The ethyl acetate layers were combined, washed with water and saturated aqueous sodium chloride in turn, dried over magnesium sulfate and evaporated in vacuo. n-Hexane was added to the oily residue and the mixture was allowed to stand in a refrigerator overnight, and triturated. The precipitates were collected by filtration to give a mixture (0.5 g.) of 7-(2-methoxyimino-3,3-ethylenedioxybutyramido)-3-methylenecepham-4-carboxylic acid (syn isomer) and 7-(2-methoxyimino-3,3-ethylenedioxybutyramido)-3-methyl-3-cephem-4-carboxylic acid (syn isomer) (5:1).

3-methylenecepham compound

N.M.R. $\delta$(DMSO-d$_6$, ppm): 1.5 (3H, s), 3.5 (2H, s), 3.8 (3H, s), 3.9 (4H, s), 5.07 (1H, s), 5.27 (2H, s), 5.3 (1H, d, J=4 Hz), 5.47 (1H, d,d, J=4 Hz, 8 Hz), 9.3 (1H, d, J=8 Hz)

Method B

Acetic acid (1 ml.) was added to a solution of 7-(2-methoxyimino-3,3-ethylenedioxybutyramido)-3-(benzothiazol-2-yl)thiomethyl-3-cephem-4-carboxylic acid (syn isomer, 500 mg.) in tetrahydrofuran (6 ml.) and water (2 ml.). Zinc powder (500 mg.) and copper sulfate 5-hydrate (50 mg.) were added to the solution at room temperature, and stirred at the same temperature for 2 hours. The resultant mixture was treated in a similar manner to that of Example 10-(3) Method A to give a mixture (120 mg.) of 7-(2-methoxyimino-3,3-ethylenedioxybutyramido)-3-methylenecepham-4-carboxylic acid (syn isomer) and 7-(2-methoxyimino-3,3-ethylenedioxybutyramido)-3-methyl-3-cephem-4-carboxylic acid (syn isomer) (5:1).

(4) 70% Aqueous perchloric acid (0.3 ml.) was added to a solution of the mixture obtained in Example 10-(3) (346 mg.) in acetone (5 ml.) and stirred at room temperature for an hour. After adding ethyl acetate (50 ml.) and water (30 ml.) to the resultant solution, the organic layer was separated. The aqueous layer was extracted with ethyl acetate (30 ml.). The organic layer and the ethyl acetate extract were combined, washed with water and saturated aqueous sodium chloride in turn, dried over magnesium sulfate and concentrated in vacuo. The residue was triturated with diisopropyl ether and the precipitates were collected by filtration to give a mixture (290 mg.) of 7-(2-methoxyimino-3-oxobutyramido)-3-methylenecepham-4-carboxylic acid (syn isomer) and 7-(2-methoxyimino-3-oxobutyramido)-3-methyl-3-cephem-4-carboxylic acid (syn isomer) (5:1).

3-methylenecepham compound

N.M.R. $\delta$(DMSO-$d_6$, ppm): 2.35 (3H, s), 3.53 (2H, s), 4.03 (3H, s), 5.1 (1H, s), 5.28 (2H, s), 5.32 (1H, d, J=5 Hz), 5.55 (1H, d,d, J=5 Hz, 8 Hz), 9.35 (1H, d, J=8 Hz)

(5) Ethyl carbazate (256 mg.) and acetic acid (0.1 ml.) were added to a solution of the mixture obtained in the Example 10-(4) (0.7 g.) in methanol (10 ml.) and stirred at 50° to 60° C. for 30 minutes. After adding ethyl acetate (50 ml.) and water (30 ml.) to the resultant solution, the mixture was acidified to pH 2.0 with 6 N-hydrochloric acid. The organic layer was separated, and the aqueous layer was extracted with ethyl acetate (30 ml.). The organic layer and the ethyl acetate extract were combined, washed with water and saturated aqueous sodium chloride in turn, dried over magnesium sulfate, and evaporated in vacuo. The residue was triturated with diisopropyl ether, and the precipitates were collected by filtration to give a mixture (0.8 g.) of 7-(2-methoxyimino-3-ethoxycarbonylhydrazonobutyramido)-3-methylenecepham-4-carboxylic acid (syn isomer) and 7-(2-methoxyimino-3-ethoxycarbonylhydrazonobutyramido)-3-methyl-3-cephem-4-carboxylic acid (syn isomer) (5:1).

3-methylenecepham compound

N.M.R. $\delta$(DMSO-$d_6$, ppm): 1.2 (3H, t, J=9 Hz), 1.95 (3H, s), 3.47 (2H, broad s), 3.82 (3H, s), 4.10 (2H, q, J=9 Hz), 5.03 (1H, s), 5.20 (2H, s), 4.83-5.5 (2H, m), 9.17 (1H, d, J=8 Hz), 10.2 (1H, s)

(6) The mixture (100 mg.) obtained in the above Example 10-(5) was dissolved in methylene chloride (16 ml.) and methanol (4 ml.). After adding acetaldehyde (45 mg.) to the solution, ozone gas was passed through the solution at −65° C. until the starting compound was undetectable on TLC, and then nitrogen gas was passed through the solution to remove the excess of ozone. Sodium borohydride was added to the solution at −65° C. until FeCl$_3$ Test became negative. The solution was allowed to stand at room temperature, and then ethyl acetate (30 ml.) and water (20 ml.) were added to the solution. After acidifying the mixture to pH 2.0 with 6 N-hydrochloric acid, the solution was saturated with sodium chloride. The aqueous layer was separated, and extracted with ethyl acetate (30 ml.). The organic layer and the ethyl acetate extract were combined, washed with water and saturated aqueous in sodium chloride in turn, dried over magnesium sulfate and evaporated in vacuo. The residue was triturated with diisopropyl ether and the precipitates were collected by filtration to give 7-(2-methoxyimino-3-ethoxycarbonylhydrazonobutyramido)-3-hydroxycepham-4-carboxylic acid (syn isomer, 42.8 mg.).

I.R. $\nu_{max}^{Nujol}$: 3700-2200, 3300, 1780 (sh), 1770, 1740, 1680, 1550 (sh), 1530, 1240, 1170, 1100, 1040

N.M.R. $\delta$(DMSO-$d_6$, ppm): 1.2 (3H, t, J=7 Hz), 1.95 (3H, s), 2.6-3.83 (3H, m), 3.83 (3H, s), 4.12 (2H, q, J=7 Hz), 4.42 (1H, d, J=6 Hz), 5.1 (1H, d, J=4 Hz), 5.43 (1H, d,d, J=4 Hz, 8 Hz), 9.11 (1H, d, J=8 Hz), 10.4 (1H, s)

(7) 70% aqueous perchloric acid (0.05 ml.) was added to a solution of 7-(2-methoxyimino-3-ethoxycarbonylhydrazonobutyramido)-3-hydroxycepham-4-carboxylic acid (syn isomer, 40 mg.) in acetone (5 ml.), and stirred at room temperature for 30 minutes. The reaction mixture was treated in a similar manner to that of Example 10-(4) to give 7-(2-methoxyimino-3-oxobutyramido)-3-hydroxycepham-4-carboxylic acid (syn isomer, 26 mg.).

I.R. $\nu_{max}^{Nujol}$: 3450, 3220, 1770 (sh), 1750 (sh), 1730, 1690, 1660, 1580, 1530, 1360, 1300, 1260, 1170, 1075, 1040 cm$^{-1}$ N.M.R. $\delta$(DMSO-$d_6$, ppm): 2.33 (3H, s), 2.67-4.0 (3H, m), 4.03 (3H, s), 4.47 (1H, d, J=6 Hz), 5.17 (1H, d, J=4 Hz), 5.49 (1H, d,d, J=4 Hz, 8 Hz), 9.3 (1H, d, J=8 Hz)

(8) Trifluoroaceticanhydride (0.2 ml.) and triethylamine (0.12 ml.) were added to a solution of 7-(2-methoxyimino-3-oxobutyramido)-3-hydroxycepham-4-carboxylic acid (syn isomer, 100 mg.) in dry tetrahydrofuran (10 ml.), and allowed to stand at room temperature for 10 minutes. Ethyl acetate (30 ml.) and water (10 ml.) were added to the reaction mixture and adjusted to pH 2 with hydrochloric acid. The ethyl acetate layer was separated, washed with water, dried over magnesium sulfate and then evaporated in vacuo. The residue was crystallized with diethyl ether to give 7-(2-methoxyimino-3-oxobutyramido)-3-cephem-4-carboxylic acid (syn isomer, 66 mg.).

I.R. $\nu_{max}^{Nujol}$: 3250, 1780, 1710, 1685, 1650, 1620 (sh), 1600, 1540, 1310, 1285, 1260, 1210, 1160, 1100, 1080, 1050, 990 cm$^{-1}$ N.M.R. $\delta$(DMSO-$d_6$, ppm): 2.30 (3H, s), 3.60 (2H, s), 4.00 (3H, s), 5.06 (1H, d, J=5 Hz), 5.79 (1H, d,d, J=5 Hz, 8 Hz), 6.48 (1H, s), 9.34 (1H, d, J=8 Hz)

(9) Aluminum chloride (120 mg.) was added to a solution of 7-(2-methoxyimino-3-oxobutyramido)-3-cephem-4-carboxylic acid (syn isomer, 50 mg.) in dry tetrahydrofuran (10 ml.). Pridinium hydrobromide perbromide (50 mg.) was added to the solution, and stirred at room temperature for 20 minutes. Ethyl acetate (50 ml.) and water (10 ml.) were added to the resultant solution and the mixture was treated in a similar manner to that of the above Example 10-(8) to give 7-(2-methoxyimino-3-oxo-4-bromobutyramido)-3-cephem-4-carboxylic acid (syn isomer, 52.5 mg.)

I.R. $\nu_{max}^{Nujol}$: 3600-2200, 3240, 1780, 1700, 1690 (sh), 1650, 1620, 1590, 1540, 1280, 1230 (sh), 1210, 1050 cm$^{-1}$ N.M.R. $\delta$(DMSO-d$_6$, ppm): 3.48, 3.73 (2H, d,d, J=9 Hz), 4.07 (2H, s), 4.12 (3H, s), 5.12 (1H, d, J=5 Hz), 5.83 (1H, d,d, J=5 Hz, 8 Hz), 6.5 (1H, s), 9.63 (1H, d, J=8 Hz)

(10) Thiourea (8.4 mg.) was added to a solution of 7-(2-methoxyimino-3-oxo-4-bromobutyramido)-3-cephem-4-carboxylic acid (syn isomer, 42 mg.) in ethanol (6 ml.) and stirred at room temperature for an hour and at 50° C. for 30 minutes. After removing ethanol from the reaction mixture in vacuo, water (5 ml.) was added to the residue and adjusted to pH 4.0 with 6 N-hydrochloric acid. The precipitates were collected by filtration and dried to give 7-[2-(2-aminothiazol-4-yl)-2-methoxyiminoacetamido]-3-cephem-4-carboxylic acid (syn isomer, 8 mg.). The filtrate was subjected to column chromatography on nonionic, adsorption resin "Diaion HP-20" (trademark: manufactured by Mitsubishi Chemical Industries Ltd., 5 ml.), washed with chilled water (5 ml.) and eluted with 20% aqueous isopropyl alcohol. The eluate was adjusted to pH 6.5 with 1 N aqueous sodium hydroxide under ice-cooling, and concentrated in vacuo. The residue was lyophilized to give sodium 7-[2-(2-aminothiazol-4-yl)-2-methoxyiminoacetamido]-3-cephem-4-carboxylate (syn isomer, 15 mg.).

I.R. $\nu_{max}^{Nujol}$: 3700-2200, 1765, 1650, 1620 (sh), 1520, 1290, 1245, 1220, 1040, 985 cm$^{-1}$ N.M.R. $\delta$(100 MHz, D$_2$O, ppm): 3.63 (2H, m), 3.99 (3H, s), 5.16 (1H, d, J=5 Hz), 5.81 (1H, d, J=5 Hz), 6.28 (1H, t), 6.96 (1H, s)

EXAMPLE 11

(1) Thionyl chloride (1.52 g.) was added to a solution of dry N,N-dimethylformamide (0.92 g.) in dry ethyl acetate (16 ml.) under ice-cooling, and stirred at the same temperature for 30 minutes. 2-Methoxyimino-3,3-ethylenedioxybutyric acid (syn isomer, 2.3 g.) was added to the solution and stirred under ice-cooling for an hour. The solution was added dropwise to a stirred solution of 7-amino-3-(5-methyl-1,3,4-thiadiazol-2-yl)thiomethyl-3-cephem-4-carboxylic acid (3.44 g.) and triethylamine (4.9 ml.) in dry methylene chloride (70 ml.) over 30 minutes and stirred at −20° to −30° C. for 1.5 hours. After adding an aqueous solution of sodium bicarbonate to the resultant solution, the aqueous layer was separated and washed with ethyl acetate. A mixed solvent (100 ml.) of ethyl acetate and methanol (4:1) was added to the aqueous solution, adjusted to pH 2.5 with 20% sulfuric acid under ice-cooling and filtered. The ethyl acetate layer was separated from the filtrate. The aqueous layer was extracted with ethyl acetate (50 ml.) twice. The ethyl acetate layer and the extract were combined, washed with water and saturated aqueous sodium chloride in turn, dried over magnesium sulfate and concentrated in vacuo. The residue was triturated with diisopropyl ether and the precipitates was collected by filtration to give 7-(2-methoxyimino-3,3-ethylenedioxybutyramido)-3-(5-methyl-1,3,4-thiadiazol-2-yl)thiomethyl-3-cephem-4-carboxylic acid (syn isomer, 2.2 g.), yellow powder.

I.R. $\nu_{max}^{Nujol}$: 3700-2100, 3300, 1780, 1730, 1680, 1630, 1535, 1240, 1200, 1170 (sh), 1100, 1080, 1040, 1000 (sh) cm$^{-1}$ N.M.R. $\delta$(DMSO-d$_6$, ppm): 1.53 (3H, s), 2.71 (3H, s), 3.75 (2H, broad s), 3.83 (3H, s), 3.97 (4H, s), 4.2, 4.57 (2H, d,d, J=13Hz), 5.13 (1H, d, J=5 Hz), 5.77 (1H, d,d, J=5 Hz, 8 Hz), 9.37 (1H, d, J=8 Hz)

(2) Zinc powder (500 mg.) and copper sulfate 5-hydrate (50 mg.) were added to a solution of 7-(2-methoxyimino-3,3-ethylenedioxybutyramido)-3-(5-methyl-1,3,4-thiadiazol-2-yl)thiomethyl-3-cephem-4-carboxylic acid (syn isomer, 500 mg.) in tetrahydrofuran (6 ml.), water (2 ml.) and acetic acid (1 ml.), and stirred at room temperature for 2 hours. The resultant mixture was filtered and washed with tetrahydrofuran (5 ml.). The filtrate and the washings were combined and treated in a similar manner to that of Example 10-(3) to give a mixture (160 mg.) of 7-(2-methoxyimino-3,3-ethylenedioxybutyramido)-5-methylenecepham-4-carboxylic acid (syn isomer) and 7-(2-methoxyimino-3,3-ethylenedioxybutyramido)-3-methyl-3-cephem-4-carboxylic acid (syn isomer).

3-methylenecepham compound

N.M.R. $\delta$(DMSO-d$_6$), ppm); 1.5 (3H, s), 3.5 (2H, s), 3.8 (3H, s), 3.9 (4H, s), 5.07 (1H, s), 5.27 (2H, s), 5.3 (1H, d, J=4 Hz), 5.47 (1H, d,d, J=4 Hz, 8 Hz), 9.3 (1H, d, J=8 Hz)

(3) Thus obtained mixture was treated in a similar manner to that of Example 10-(4) to (9) to give 7-(2-methoxyimino-3-oxo-4-bromobutyramido)-3-cephem-4-carboxylic acid (syn isomer).

I.R. $\nu_{max}^{Nujol}$: 3600-2200, 3240, 1780, 1700, 1690 (sh), 1650, 1620, 1590, 1540, 1280, 1230 (sh), 1210, 1050 cm$^{-1}$ N.M.R. $\delta$(DMSO-d$_6$, ppm): 3.48, 3.73 (2H, d,d, J=9 Hz), 4.07 (2H, s), 4.12 (3H, s), 5.12 (1H, d J=5 Hz), 5.83 (1H, d,d, J=5 Hz, 8 Hz), 6.5 (1H, s), 9.63 (1H, d, J=9 Hz)

EXAMPLE 12

(1) Method A

Zinc powder (3.44 g.) was added to a stirred solution of 7-amino-3-(5-methyl-1,3,4-thiadiazol-2-yl)-thiomethyl-3-cephem-4-carboxylic acid (3.44 g.) in acetone (60 ml.) and 6 N-hydrochloric acid (25 ml.), and stirred at room temperature for an hour. The resultant mixture was filtered and washed with water. The filtrate and the washings were combined and washed with ethyl acetate (30 ml.) twice. The aqueous solution was adjusted to pH 7.5 with 4 N-aqueous sodium hydroxide, which contained a mixture of 7-amino-3-methylenecepham-4-carboxylic acid and 7-amino-3-methyl-3-cephem-4-carboxylic acid. On the other hand, thionyl chloride (1.52 g.) was added to a solution of dry N,N-dimethylformamide (0.92 g.) in dry ethyl acetate (16 ml.) under ice-cooling, and stirred at 0° to 5° C. for 30 minutes. 2-Methoxyimino-3,3-ethylenedioxybutyric acid (syn isomer) (2.3 g.) was added to the suspension. The solution was added to the above solution under ice-cooling, and stirred at the same temperature for 2 hours while adjusting pH 7.0 to 7.5 with 4 N aqueous sodium hydroxide. After removing the solvent from the resultant solution in vacuo, ethyl acetate (100 ml.) was added to a residue. The solution was adjusted to pH 2.0 with 6 N hydrochloric acid, and the organic layer was separated. The aqueous layer was extracted with ethyl acetate (50 ml.) twice, and the organic layer and the extract were combined, washed with water and saturated aqueous sodium chloride in turn, dried over magnesium sulfate and then concentrated in vacuo. The residue was triturated with diisopropyl ether and the precipitates were collected by filtration to give a mixture (1.59 g.) of 7-(2-methoxyimino-3,3-ethylenedioxybutyramido)-3-methylenecepham-4-carboxylic acid (syn isomer) and 7-(2-methoxyimino-3,3-ethylenedioxybutyramido)-3-methyl-3-cephem-4-carboxylic acid (syn isomer).

3-methylenecepham compound

N.M.R. $\delta$(DMSO-$d_6$, ppm): 1.5 (3H, s), 3.5 (2H, s), 3.8 (3H, s), 3.9 (4H, s), 5.07 (1H, s), 5.27 (2H, s), 5.3 (1H, d, J=4 Hz), 5.47 (1H, d,d, J=4 Hz, 8 Hz), 9.3 (1H, d, J=8 Hz)

(2) Method B

P-Toluene-sulfonic acid hydrate (11.4 g.) was added to a solution of 7-amino-3-(5-methyl-1,3,4-thiadiazol-2-yl)thiomethyl-3-cephem-4-carboxylic acid (3.44 g.) in water (60 ml.). To the solution was added zinc powder (3.4 g.), and the mixture was stirred at room temperature for an hour. The resultant mixture was filtered and washed with water (10 ml.). The filtrate and the washings were combined, washed with ethyl acetate (90 ml.), and adjusted to pH 7.0 with 4 N aqueous sodium hydroxide. To the aqueous solution was added acetone (40 ml.) and the mixture was treated with the activated acid solution of 2-methoxyimino-3,3-ethylenedioxybutyric acid (syn isomer) obtained in a similar manner to that of Example 12-(1) A Method. Ethyl acetate (100 ml.) was added to the reaction mixture and adjusted to pH 2.0 with 6 N hydrochloric acid. The ethyl acetate layer was separated, and the aqueous layer was extracted with ethyl acetate (50 ml.) twice. The ethyl acetate layer and the extract were combined, washed with saturated aqueous sodium chloride, dried over magnesium sulfate and then evaporated in vacuo. The oily residue was washed with diisopropyl ether to give a mixture of 7-(2-methoxyimino-3,3-ethylenedioxybutyramido)-3-methylenecepham-4-carboxylic acid (syn isomer) and 7-(2-methoxyimino-3,3-ethylenedioxybutyramido)-3-methyl-3-cephem-4-carboxylic acid (syn isomer).

3-methylenecepham compound

N.M.R. $\delta$(DMSO-$d_6$, ppm): 1.5 (3H, s), 3.5 (2H, s), 3.8 (3H, s), 3.9 (4H, s), 5.07 (1H, s), 5.27 (2H, s), 5.3 (1H, d, J=4 Hz), 5.47 (1H, d,d, J=4 Hz), 8 Hz), 9.3 (1H, d, J=8 Hz)

(3) The mixture obtained in the above Example 12-(2) B method was dissolved in acetone (50 ml.), and 70% aqueous perchloric acid (0.3 ml.) was added to the solution and stirred at room temperature for 1.5 hours. Ethyl acetate (100 ml.) and water (50 ml.) were added to the resultant solution. The ethyl acetate layer was separated and the aqueous layer was extracted with ethyl acetate (50 ml.) twice. The ethyl acetate layer and the extract were combined, washed with water and saturated aqueous sodium chloride in turn, dried over magnesium sulfate and then evaporated in vacuo. The residue was triturated with diisopropyl ether and the precipitates were collected by filtration and dried to give a mixture (2.1 g.) of 7-(2-methoxyimino-3-oxobutyramido)-3-methylenecepham-4-carboxylic acid (syn isomer) and 7-(2-methoxyimino)-3-oxobutyramido)-3-methyl-3-cephem-4-carboxylic acid (syn isomer).

3-methylenecepham compound

N.M.R. $\delta$(DMSO-$d_6$, ppm): 2.35 (3H, s), 3.53 (2H, s), 4.03 (3H, s), 5.1 (1H, s), 5.28 (2H, s), 5.32 (1H, d, J=5 Hz), 5.55 (1H, d,d, J=5 Hz, 8 Hz), 9.35 (1H, d, J=8 Hz)

(4) Thus obtained mixture was treated in a similar manner to that of Example 10-(5) to (9) to give 7-(2-methoxyimino-3-oxo-4-bromobutyramido)-3-cephem-4-carboxylic acid (syn isomer).

I.R. $\nu_{max}^{Nujol}$: 3600-2200, 3240, 1780, 1700, 1690 (sh), 1650, 1620, 1590, 1540, 1280, 1230 (sh), 1210, 1050 cm$^{-1}$ N.M.R. $\delta$(DMSO-$d_6$, ppm): 3.48, 3.73 (2H, d,d J=9 Hz), 4.07 (2H, s), 4.12 (3H, s), 5.12 (1H, d, J=5 Hz), 5.83 (1H, d,d, J=5 Hz, 8 Hz), 6.5 (1H, s), 9.63 (1H, d, J=8 Hz)

EXAMPLE 13

(1) 2-Methoxyimino-3,3-ethylenedioxybutyric acid (syn isomer, 15.1 g.) and 7-amino-3-(1,3,4-thiadiazol-2-yl)thiomethyl-3-cephem-4-carboxylic acid (29.1 g.) were treated in a similar manner to that of Example 10-(2) to give 7-(2-methoxyimino-3,3-ethylenedioxybutyramido)-3-(1,3,4-thiadiazol-2-yl)thiomethyl-3-cephem-4-carboxylic acid (syn isomer, 32.5 g.). Mp. 145° to 152° C. (dec.).

I.R. $max^{Nujol}$: 3350, 1770, 1730, 1665, 1620, 1530 cm$^{-1}$

N.M.R. $\delta$(DMSO-$d_6$, ppm): 1.53 (3H, s), 3.72 (2H, broad s), 3.82 (3H, s), 3.95 (4H, s), 4.45 (2H, $AB_q$, J=13 Hz), 5.15 (1H, d, , J=5 Hz), 5.77 (1H, d,d, J=5 Hz, 8 Hz), 9.38 (1H, d, J=8 Hz), 9.58 (1H, s)

(2) Thus obtained compound was treated in a similar manner to that of Example 10-(3) to (9) to give 7-(2-methoxyimino-3-oxo-4-bromobutyramido)-3-cephem-4-carboxylic acid (syn isomer).

I.R. $\nu_{max}^{Nujol}$. 3600–2200, 3240, 1780, 1700, 1690 (sh), 1650, 1620, 1590, 1540, 1280, 1230 (sh), 1210, 1050 cm$^{-1}$ N.M.R. $\delta$(DMSO-$d_6$, ppm): 3.48, 3.73 (2H, d,d, J=9 Hz), 4.07 (2H, s), 4.12 (3H, s), 5.12 (1H, d, J=5 Hz), 5.83 (1H, d,d, J=5 Hz, 8 Hz), 6.5 (1H, s), 9.63 (1H, d, J=8 Hz)

EXAMPLE 14

(1) Conc. Hydrochloric acid (2325 ml.) and zinc powder (585 g.) were added to a suspension of 7-amino-3-(5-methyl-1,3,4-thiadiazol-2-yl)thiomethyl-3-cephem-4-carboxylic acid (1000 g.) in water (10 l.) under ice cooling and then stirred at 10° to 15° C. for 1.5 hours. After removal of the zinc powder from the resultant mixture by filtration, the filtrate was adjusted to pH 2.0 and washed with ethyl acetate (5 l.) The solution was adjusted to pH 7.0 with 8 N sodium hydroxide solution and allowed to stand in refrigerator overnight. The insoluble substance was removed from the mixture. The filtrate was concentrated to the volume of 5 l. in vacuo.

The solution was adjusted to pH 3.5 with conc. hydrochloric acid. The precipitates were collected by filtration, and washed with water (1 l.), acetone (1 l.), ethanol (700 ml.) and diethyl ether (1 l.) in turn to give 7-amino-3-methylenecepham-4-carboxylic acid (423.7 g.)

N.M.R. $\delta$($N_aHCO_3+D_2O$, ppm): 3.37, 3.72 (d., d., 2H, J=14 Hz), 5.00: (S., 1H), 5.28, 5.35 (S.S., 2H), 5.33: (d., 1H, J=3 Hz), 5.42: (d., 1H, J=3 Hz).

(2) 7-Amino-3-methylenecepham-4-carboxylic acid (10.7 g.) was suspended in methanol (300 ml.) and dissolved by adding methanolic hydrochloric acid (300 ml.). After adding acetaldehyde (11.3 ml.) to the solution at −65° C., ozone was bubbled into the solution. The excess of ozone was removed by introduction of nitrogen gas. To a solution of sodium borohydride (5.67 g.) in a sodium chloride saturated aqueous solution (400 ml.) was added the resultant solution under cooling and allowed to stand at 5° C. overnight. After evaporating methanol from the solution, water (100 ml.) was added to the residue and adjusted to pH 5.0. The solution was subjected to column chromatography on nonionic adsorption resin "Diaion HP-20" (trademark: manufactured by Mitsubishi Chemical Industries Ltd.). After the eluate was concentrated in vacuo, the residue was lyophilized and suspended in methanol (50 ml.). The suspension was filtered and the filtrate was evaporated. The residue was pulverized with acetone, collected by filtration and washed with acetone to give sodium 7-amino-3-hydroxycepham-4-carboxylate (3.1 g.).

I.R. $\nu_{max}^{Nujol}$: 3700–2400, 1755, 1620 cm$^{-1}$

N.M.R. $\delta$(D$_2$O+DCl,ppm): 5.37 (1H, d., J=4 Hz), 4.93 (1H, d., J=4 Hz), 4.78 (1H, d., J=6 Hz), 4.63 (1H, m), 3.01 (1H, s), 3.10 (1H, d., J=3 Hz).

EXAMPLE 15

(1) A methanolic hydrochloric acid (20% w/w, 1.8 g.) and acetaldehyde (1.76 g.) were added to a suspension of 7-amino-3-methylenecepham-4-carboxylic acid (2.14 g.) in dry methanol (100 ml.) and stirred at room temperature. Ozone was bubbled in the solution until the starting compound is not detected. Excess of ozone was excluded by introducing nitrogen gas into the resultant solution. The solution was added to a solution of sodium borohydride (1.14 g.) in sodium chloride saturated aqueous solution (160 ml.), allowed to stand in refrigerator overnight, and then acetone (80 ml.) was added to the solution under ice cooling [Solution A]. On the other hand, 2-methoxyimino-3,3-ethylenedioxybutyric acid (syn isomer, 1.89 g.) was added to a suspension of Vilsmeier reagent made from N,N-dimethylformamide (1.42 ml.) and thionyl chloride (1.32 ml.) in dry ethyl acetate (10 ml.) under cooling and stirred for 30 minutes at pH 7.0 to 7.5 to give an active acid solution. The solution was added to the solution [Solution A] under ice-cooling and stirred at pH 7.0 to 7.5 for an hour. After removing acetone in vacuo, the remaining solution was washed with ethyl acetate (50 ml.) and an aqueous layer was separated. Ethyl acetate (100 ml.) was added to the aqueous solution, saturated with sodium chloride and adjusted to pH 2.0 with 6 N hydrochloric acid. The ethyl acetate layer was separated, washed with sodium chloride saturated aqueous solution and dried over magnesium sulfate. After concentrating the solution in vacuo, the residue was pulverized with diisopropyl ether. The precipitates were collected by filtration and dried to give 7-(3,3-ethylenedioxy-2-methoxyiminobutyramido)-3-hydroxy-cepham-4-carboxylic acid (syn isomer, 210 mg.)

I.R. $\nu_{max}^{Nujol}$: 3700–2200 (br), 1760, 1660, 1520, 1200, 1040 cm$^{-1}$ N.M.R. $\delta$(DMSO-d$_6$): 1.5 (3H, s), 2.67–4.00 (3H, m), 3.77 (3H, s), 3.90 (4H, s), 4.43 (1H, d, J=6 Hz), 5.12 (1H, d, J=4 Hz), 5.42 (1H, dd, J=4 Hz, 8 Hz), 9.17 (1H, d, J=8 Hz)

(2) Trifluoroacetic anhydride (0.1 ml.) and triethylamine (0.2 ml.) were added to a solution of 7-(2-methoxyimino-3,3-ethylenedioxybutyramido)-3-hydroxycepham-4-carboxylic acid (syn isomer, 50 mg.) in dry tetrahydrofuran (5 ml.) and stirred at room temperature for 10 minutes. A sodium bicarbonate aqueous solution (2 ml.) was added to the resultant solution and heated for two minutes. Ethyl acetate and water were added to the solution, acidified with 6 N hydrochloric acid and extracted with ethyl acetate. The aqueous layer was extracted with ethyl acetate. The ethyl acetate layer and extract were combined together, washed with water and a sodium chloride aqueous solution in turn and dried over magnesium sulfate. The solution was evaporated in vacuo, and the residue was pulverized with diethyl ether to give 7-(2-methoxyimino-3,3-ethylenedioxybutyramido)-3-cepham-4-carboxylic acid (syn isomer, 30 mg.)

I.R. $_{max}^{Nujol}$: 3300, 1790, 1730, 1700, 1650, 1550, 1470 cm$^{-1}$

N.M.R. (DMSO-d$_6$, ppm): 1.55 (3H, s), 3.50–3.73 (2H, broad s), 3.83 (4H, s), 3.97 (3H, s), 5.10 (1H, d, J=4 Hz), 6.83 (1H, d,d, J=4 Hz, 8 Hz), 6.40–6.63 (1H, t), 9.35 (1H, d, J=8 Hz)

(3) 70% Perchloric acid (1.09 ml.) was added to a solution of 7-(2-methoxyimino-3,3-ethylenedioxybutyramido)-3-cephem-4-carboxylic acid (syn isomer, 10.9 g.) in acetone (270 ml.) and stirred at room temperature for 3 hours. Water (150 ml.) was added to the resultant solution and acetone was removed in vacuo. Ethyl acetate (300 ml.) was added to the residue and the ethyl acetate layer was separated. The aqueous layer was extracted with ethyl acetate (400 ml.) and then the ethyl acetate extract was combined with ethyl acetate layer. The organic solution was washed with a sodium chloride saturated aqueous solution, allowed to stand in refrigerator overnight and dried over magnesium sulfate. The solution was concentrated in vacuo and the residue was pulverized with diisopropyl ether to give 7-(2-methoxyimino-3-oxobutyramido)-3-cephem-4-carboxylic acid (syn isomer, 5.75 g.).

I.R. $\nu_{max}$: 3250, 1780, 1710, 1685, 1650, 1620(sh), 1600, 1540 cm$^{-1}$

N.M.R. $\delta$(DMSO-d$_6$, ppm): 2.30 (S., 3H), 3.6 (br. S., 2H), 4.0 (S., 3H), 5.06 (d., 1H, J=5 Hz), 5.79 (d. d., 1H, J=5 Hz, 8 Hz), 6.48 (t., 1H, J=4), 9.34 (d., 1H, J=8 Hz).

EXAMPLE 16

(1) Trifluoroacetic anhydride (6.8 ml.) and triethylamine (4.2 ml.) were added to a solution of 7-(3-ethoxycarbonylhydrazono-2-methoxyiminobutyramido)-3-hydroxycepham-4-carboxylic acid (syn isomer, 4.3 g.) in dry tetrahydrofuran (215 ml.) under ice cooling and stirred at the same temperature for an hour. To the resultant solution were added ethyl acetate (200 ml.) and a sodium chloride saturated aqueous solution (100 ml.), and adjusted to pH 2.0 with 6 N hydrochloric acid. After separating the organic layer, the aqueous layer was extracted with ethyl acetate (100 ml.). The organic layer and the extract were combined; washed with a sodium chloride saturated aqueous solution and dried over magnesium sulfate. The solution was evaporated in vacuo, and diisopropyl ether (50 ml.) was added to the residue. The precipitates were collected by filtration and washed with diisopropyl ether to give 7-(3-ethoxycarbonylhydrazono-2-methoxyiminobutyramido)-3-cephem-4-carboxylic acid (syn isomer, 3.85 g.).

I.R. $\nu_{max}^{Nujol}$: 3300, 1780, 1730, 1680, 1530 cm$^{-1}$

N.M.R. $\delta$(DMSO-d$_6$, ppm): 1.23 (3H, t, J=7 Hz), 2.00 (3H, s), 3.90 (3H, s), 4.18 (2H, q, J=7 Hz), 5.08 (1H, d, J=4 Hz), 5.83 (1H, d,d, J=4 Hz, 8 Hz), 6.38–6.62 (1H, t), 9.22 (1H, d, J=8 Hz), 10.30 (1H, s)

(2) 70% Perchloric acid (4.1 ml.) was added to a solution of 7-(3-ethoxycarbonylhydrazono-2-methoxyiminobutyramido)-3-cephem-4-carboxylic acid (syn isomer, 4.1 g.) at room temperature and stirred at the same temperature for 2 hours. After adjusting to pH 2.0 with 1 N sodium hydroxide aq. acetone was evaporated in vacuo from the resultant solution. Ethyl acetate (100 ml.) and a sodium chloride saturated aqueous solution (50 ml.) to the residue and the ethyl acetate layer was separated. The aqueous layer was extracted with ethyl acetate (100 ml.) and combined with the ethyl acetate layer. The solution was washed with a sodium chloride saturated aqueous solution, dried over magnesium sulfate and evaporated in vacuo. The residue was pulverized with diisopropyl ether and the precipitates were collected by filtration to give 7-(2-methoxyimino-3-oxobutyramido)-3-cephem-4-carboxylic acid (syn isomer, 3.25 g.).

I.R. $\nu_{max}^{Nujol}$: 3250, 1780, 1710, 1685, 1650, 1620 (sh), 1600, 1540 cm$^{-1}$ N.M.R. $\delta$(DMSO-d$_6$, ppm): 2.30 (3H, s), 3.60 (2H, s), 4.00 (3H, s), 5.06 (1H, d, J=5 Hz), 5.79 (1H, dd, J=5 Hz, 8 Hz), 6.48 (1H, s), 9.34 (1H, d, J=8 Hz)

EXAMPLE 17

Zinc powder (40 g) was added to a solution of 7-aminocephalosporanic acid (27.3 g) and conc. hydrochloric acid (70 ml.) in water (200 ml.) for 5° C. and stirred for an hour. The resultant solution was adjusted to pH 4.0 with 4 N sodium hydroxide and concentrated to 100 ml. of the volume. After adjusting the solution to pH 4.0, the solution was allowed to stand under cooling overnight. The precipitates were collected by filtration to give 7-amino-3-methylenecepham-4-carboxylic acid (11.96 g.).

I.R. $\nu_{max}^{Nujol}$: 3200–2000, 1770, 1620 (sh), 1540 (sh), 1460, 1220, 1140 cm$^{-1}$ N.M.R. $\delta$(NaHCO$_3$-D$_2$O, ppm): 3.37, 3.72 (2H, d, J=14 Hz), 5.00 (1H, s), 5.28 (1H, s), 5.33 (1H, d, J=3 Hz), 5.35 (1H, s), 5.42 (1H, d, J=3 Hz)

EXAMPLE 18

Trifluoroacetic anhydride (1 ml.), anisole (1 drop) and dimethylformamide (1 drop) were added to a solution of 7-(2-methoxyimino-3-oxo-4-bromobutyramido)-3-hydroxycepham-4-carboxylic acid (syn isomer, 1 g.) in dry tetrahydrofuran (3 ml.) and stirred for 4 hours. After adding methanol (0.3 ml.) into the resultant solution, the solution was stirred for an hour and concentrated in vacuo. The residue was pulverized with diisopropyl ether. The precipitates were collected by filtration and dried over phosphorus pentoxide to give 7-(2-methoxyimino-3-oxo-4-bromobutyramido)-3-cephem-4-carboxylic acid (syn isomer, 0.82 g).

I.R. $\nu_{mad}^{Nujol}$: 3600–2200, 3240, 1780, 1700, 1690 (sh), 1650, 1620, 1590, 1540, 1280, 1230 (sh), 1210, 1050 cm$^{-1}$ N.M.R. $\delta$(DMSO-d$_6$, ppm): 3.57 (2H, d, J=4 Hz), 4.57 (2H, s), 4.05 (3H, s), 5.05 (1H, d, J=5 Hz), 5.78 (1H, d,d, J=5 Hz, 8 Hz), 6.50 (1H, s), 9.63 (1H, d, J=8 Hz)

EXAMPLE 19

Trifluoroacetic anhydride (1 ml.) was added to a solution of 7-(2-methoxyimino-3-oxo-4-bromobutyramido)-3-hydroxycepham-4-carboxylic acid (syn isomer, 1 g.) in tetrahydrofuran (3 ml.) and the mixture was treated in a similar manner to that of Example 18 to give 7-(2-methoxyimino-3-oxo-4-bromobutyramido)-3-cephem-4-carboxylic acid (syn isomer, 0.65 g.).

I.R. $\nu_{max}^{Nujol}$: 3600–2200, 3240, 1780, 1700, 1690 (sh), 1650, 1620, 1590, 1540, 1280, 1230 (sh), 1210, 1050 cm$^{-1}$ N.M.R. $\delta$(DMSO-d$_6$, ppm): 3.57 (2H, d, J=4 Hz), 4.57 (2H, s), 4.05 (3H, s), 5.05 (1H, d, J=5 Hz), 5.78 (1H, d,d, J=5 Hz, 8 Hz), 6.50 (1H, s), 9.63 (1H, d, J=8 Hz)

EXAMPLE 20

7-Amino-3-methylenecepham-4-carboxylic acid (107 g.) was dissolved in a solution of methanol (6.4 l.) and methanesulfonic acid (57.7 g.). Ozone was bubbled into the solution at −70° to −75° C. until the starting compound was not detected. After bubbling nitrogen gas into the resultant mixture, sodium methoxide (3.5 g.) was added to the mixture below −65° C. Sodium borohydride (56.7 g.) was added to a solution of sodium hydroxide (14.4 g.) in water (3.2 l), stirred at room temperature for 20 minutes and chilled. The oxidized reaction mixture was added to the sodium borohydride solution over 3 minutes, and stirred at −4° to 0° C. for 20 minutes. The solution was adjusted to pH 4.0 with 6 N hydrochloric acid, and allowed to stand at 5° C. overnight. The precipitates were collected by filtration, washed with methanol and then dried to give 7-amino-3-hydroxycepham-4-carboxylic acid (70.8 g.).

I.R. $\nu_{max}^{Nujol}$: 3500, 2700–2000 (broad), 1760, 1620, 1580 cm$^{-1}$

N.M.R. $\delta$(D$_2$O+DCl, ppm): 5.37 (1H, d, J=4 Hz), 4.93 (1H, d, J=4 Hz), 4.78 (1H, d, J=6 Hz), 4.63 (1H, m), 3.01 (1H, s), 3.10 (1H, d, J=3 Hz)

EXAMPLE 21

Phosphorus oxychloride (0.54 ml.), N,N-dimethylformamide (438 mg.), 2-methoxyimino-3,3-ethylenedioxy-4-bromobutyric acid (syn isomer, 1.6 g.), 7-amino-3-cephem-4-carboxylic acid (1 g.), trimethylsilylacetamide (3.3 g.) and dry ethyl acetate (21 ml.) were treated in a similar manner to that of Example 11 (1) to give 7-(2-methoxyimino-3,3-ethylenedioxy-4-bromobutyramido)-3-cephem-4-carboxylic acid (syn isomer, 2.25 g.)

I.R. $\nu_{max}^{Nujol}$: 3350, 1780, 1730, 1680, 1640 (shoulder), 1540, 1295, 1220, 1170, 1100, 1040 cm$^{-1}$ N.M.R. $\delta$(DMSO-d$_6$, ppm): 3.6 (2H, d, J=4 Hz), 3.83 (5H, s), 4.05 (4H, s), 5.1 (1H, d, J=4 Hz), 5.8 (1H, dd, J=4 Hz, 8 Hz), 6.52 (1H, t, J=4 Hz), 9.47 (1H, d, J=8 Hz)

EXAMPLE 22

7-(2-Methoxyimino-3-oxo-4-bromobutyramido)-3-hydroxycepham-4-carboxylic acid (syn isomer, 10 g.) was added to dry tetrahydrofuran (100 ml.) at 30° C. To the solution was added acetic anhydride (10 ml.) and stirred at the same temperature for 30 minutes. Sodium acetate (3 g.) was added to the solution and stirred at 30° C. for 4 hours. 6 N Hydrochloric acid (10 ml) was dropwise added to the reaction mixture under ice-cooling and the solvent was evaporated in vacuo below 30° C. After adding water into the residue, the mixture was stirred at 20° to 25° C. for 30 minutes. The precipitates were collected by filtration, washed with water and dried to give 7-(2-methoxyimino-3-oxo-bromobutyramido)-3-cephem-4-carboxylic acid (syn isomer, 7 g.).

I.R. $\nu_{max}^{Nujol}$: 3600–2200, 3240, 1780, 1700, 1690 (sh), 1650, 1620, 1590, 1540, 1280, 1230 (sh), 1210, 1050 cm$^{-1}$ N.M.R. δ(DMSO-d$_6$, ppm): 3.57 (2H, d, J=4 Hz), 4.57 (2H, s), 4.05 (3H, s), 5.05 (1H, d, J=5 Hz), 5.78 (1H, dd, J=5 Hz, 8 Hz), 6.50 (1H, s), 9.63 (1H, d, J=8 Hz).

EXAMPLE 23

7-(2-Methoxyimino-3-oxo-4-bromobutyramido)-3-cephem-4-carboxylic acid (syn isomer, 10 g.) was added to a solution of thiourea (2.81 g.) and sodium acetate (2.22 g.) in methanol (50 ml) and stirred at 30° C. for 5 hours. To the resultant solution was added diisopropyl ether (200 ml.) and stirred at 30 minutes. The precipitates were collected by filtration, washed with diisopropyl ether and dried to give 7-[2-(2-aminothiazol-4-yl)-2-methoxyiminoacetamido]-3-cephem-4-carboxylic acid (syn isomer, 11.2 g.).

I.R. $\nu_{max}^{Nujol}$: 3700–2200, 1765, 1650, 1620 (sh), 1520, 1290, 1245, 1220, 1040, 985 cm$^{-1}$ N.M.R. δ(D$_2$O, ppm): 3.63 (2H, m), 3.99 (3H, s), 5.16 (1H, d, J=5 Hz), 5.81 (1H, d, J=5 Hz), 6.28 (1H, t), 6.96 (1H, s).

EXAMPLE 24

7-(2-Methoxyimino-3-oxo-4-bromobutyramido)-3-hydroxycepham-4-carboxylic acid (syn isomer, 2.1 g.) was dissolved in a solution of N,N-dimethylformamide (0.8 ml.) and tetrahydrofuran (7.6 ml). To the solution was added a solution of N,N-dimethylformamide (0.78 ml) and phosphorus oxychloride (0.9 ml) in tetrahydrofuran (0.7 ml) all at once at −5° C., and stirred at the same temperature for 30 minutes and at 22° C. for 30 minutes. The resultant solution was poured into ice water. The precipitates were washed with water (50 ml) and diisopropyl ether (25 ml) and dried over phosphorus pentoxide to give 7-(2-methoxyimino-3-oxo-4-bromobutyramido)-3-cephem-4-carboxylic acid (syn isomer, 1.37 g.). The mother liquid was extracted with ethyl acetate (100 ml.). The extract was washed with water and dried over magnesium sulfate. The solution was concentrated in vacuo and the precipitates were pulverized with diisopropyl ether to give the same objective compound (syn isomer, 0.2 g.). Similar result was obtained by using SOCl$_2$ in stead of POCl$_3$.

I.R. $\nu_{max}^{Nujol}$: 3600–2200, 3240, 1780, 1700, 1690 (sh), 1650, 1620, 1590, 1540, 1280, 1230 (sh), 1210, 1050 cm$^{-1}$ N.M.R. δ(DMSO-d$_6$, ppm): 3.57 (2H, d, J=4 Hz), 4.57 (2H, s), 4.05 (3H, s), 5.05 (1H, d, J=5 Hz), 5.78 (1H, dd, J=5 Hz, 8 Hz), 6.50 (1H, s), 9.63 (1H, d, J=8 Hz),

EXAMPLE 25

(1) Phosphorus oxychloride (0.5 ml.) was added to a solution of N,N-dimethylformamide (0.42 ml) in dry ethyl acetate (1 ml.) under cooling, and 2-methoxyimino-3,3-ethylenedioxy-4-bromobutyric acid (syn isomer, 1.2 g.) was added thereto under cooling and stirred at the same temperature. The solution was added to a stirred solution of 7-amino-3-hydroxycepham-4-carboxylic acid (1.0 g.) and trimethylsilylacetamide (6.0 g.) in dry ethyl acetate (50 ml.), at −20° C. and stirred at the same temperature for an hour. Ethyl acetate (20 ml.) and water (10 ml) were added to the resultant solution and the ethyl acetate layer was separated. The aqueous layer was extracted with ethyl acetate (20 ml.). The ethyl acetate layer and the extract were combined, and extracted with a saturated aqueous solution of sodium bicarbonate (20 ml.), and water (20 ml.) successively. After ethyl acetate (50 ml) was added thereto, the aqueous solution was adjusted to pH 2.0 with 6 N hydrochloric acid, and the ethyl acetate layer was separated. The aqueous layer was extracted with ethyl acetate (25 ml×2). The ethyl acetate layer and the extract were combined, washed with a saturated sodium chloride aqueous solution and dried over magnesium sulfate. After evaporating the solvent in vacuo, the residue was pulverized with diisopropyl ether. The precipitates were collected by filtration to give 7-(2-methoxyimino-3,3-ethylenedioxy-4-bromobutyramido)-3-hydroxycepham-4-carboxylic acid (syn isomer, 1.8 g.).

I.R. (Nujol): 3300, 3100–2200 (broad), 1760, 1660, 1530, 1210, 1040, 950 cm$^{-1}$ N.M.R. δ(DMSO-d$_6$+D$_2$O, ppm): 2.75–4.17 (3H, m), 3.83 (5H, s), 4.08 (4H, s), 4.50 (1H, d, J=6 Hz), 5.17 (1H, d, J=4 Hz), 5.47 (1H, dd, J=4 Hz, 8 Hz), 9.37 (1H, d, J=8 Hz)

(2) 7-[2-Methoxyimino-3,3-ethylenedioxy-4-bromobutyramido)-3-hydroxycepham-4-carboxylic acid (syn isomer, 1 g.), 70% aqueous hydroperchloric acid (0.2 ml.) and acetic acid (2 ml.) were treated in a similar manner to that of Example 10 (4) to give 7-[2-methoxyimino-3-oxo-4-bromobutyramido)-3-hydroxycepham-4-carboxylic acid (syn isomer, 0.6 g.).

I.R. (Nujol): 3460, 3280, 3200–2200, 1780, 1730, 1710, 1660, 1590, 1560, 1240, 1060

N.M.R. δ(DMSO-d$_6$, ppm): 2.67–4.17 (3H, m), 4.08 (3H, s), 4.50 (1H, d, J=6 Hz), 4.67 (2H, s), 5.20 (1H, d, J=4 Hz), 5.53 (1H, dd, J=4 Hz, 8 Hz), 9.40 (1H, d, J=8 Hz).

EXAMPLE 26

7-Amino-3-hydroxycepham-4-carboxylic acid (2.18 g, purity 84.8%), trimethylsilylacetamide (10.5 g.), 2-methoxyimino-3,3-dimethoxy-4-bromobutyric acid (syn isomer, 3.24 g.), N,N-dimethylformamide (1.1 ml), phosphorus oxychloride (1.36 ml) and methylene chloride (50 ml.) were treated in a similar manner to that of Example 25 (1) to give 7-[2-methoxyimino-3,3-dimethoxy-4-bromobutyramido]-3-hydroxycepham-4-carboxylic acid (syn isomer, 3.75 g.).

I.R. (Nujol): 3700–3100 (broad) 3100–2700 (broad), 2600, 1780, 1680, 1540 cm$^{-1}$ N.M.R. δ(DMSO-d$_6$+D$_2$O, ppm): 2.6–4.17 (3H, m), 3.27 (6H, s), 3.77 (2H, s), 3.88 (3H, s), 4.48 (1H, d, J=6 Hz), 5.17 (1H, d, J=4 Hz), 5.48 (1H, dd, J=4 Hz, 8 Hz), 8.87 (1H, d, J=8 Hz)

EXAMPLE 27

Trifluoroacetic anhydride (0.5 ml.) was added to a solution of 7-(2-methoxyimino-3-oxo-4-bromobutyramido)-3-hydroxycepham-4-carboxylic acid (syn isomer, 180 mg.) in dry tetrafuran (10 ml.) and stirred at room temperature for 10 minutes. Triethylamine (0.2 ml.) was added to the resultant solution and stirred at room temperature for 10 minutes. Ethyl acetate was added to the solution and adjusted to pH 2.0 with 6 N hydrochloric acid. The solution was washed with water and a sodium chloride saturated aqueous solution successively and dried over magnesium sulfate. After the solution was concentrated in vacuo, the residue was pulverized with diisopropyl ether to give 7-(2-methoxyimino-3-oxo-4-bromobutyramido)-3-cephem-4-carboxylic acid (syn isomer, 171.5 mg.).

I.R. $\nu_{max}^{Nujol}$: 3600–2200, 3240, 1780, 1700, 1690 (sh), 1650, 1620, 1590, 1540, 1280, 1230 (sh), 1210, 1050 cm$^{-1}$ N.M.R. δ(DMSO-d$_6$, ppm): 3.57 (2H, d, J=4 Hz), 4.57 (2H, s), 4.05 (3H, s), 5.05 (1H, d, J=5 Hz), 5.78 (1H, d,d, J=5 Hz, 8 Hz), 6.50 (1H, s), 9.63 (1H, d, J=8 Hz)

EXAMPLE 28

7-Amino-3-hydroxycepham-4-carboxylic acid (1.09 g., purity 84.8%), trimethylsilylacetamide (5.3 g.), 2-methoxyimino-3,3-diethoxy-4-bromobutyric acid (syn isomer, 1.8 g.), phosphorus oxychloride (0.68 ml.), N,N-dimethylformamide (0.55 ml.) and methylene chloride (25 ml.) were treated in a similar manner to that of Example 25 (1) to give 7-(2-methoxyimino-3,3-diethoxy-4-bromobutyramido)-3-hydroxycepham-4-carboxylic acid (syn isomer, 1.1 g.).

I.R. (film) ν: 3600–3100, 2950, 1780–1700, 1700–1620, 1520 cm$^{-1}$

N.M.R. δ(DMSO-d$_6$, ppm): 1.08, (3H, t, J=8 Hz), 1.13 (3H, t, J=8 Hz), 3.50 (2H, q, J=8 Hz), 3.57 (2H, q, J=8 Hz), 2.90–4.20 (3H, m), 3.66 (2H, s), 3.78 (3H, s), 4.38 (1H, d, J=6 Hz), 5.08 (1H, d, J=8 Hz), 5.38 (1H, dd, J=4 Hz, 8 Hz), 8.57 (1H, d, J=8 Hz).

EXAMPLE 29

7-Amino-3-hydroxycepham-4-carboxylic acid (10.9 g, purity 84.8%), 2-methoxyimino-3,3,diethoxy-4-bromobutyric acid (syn isomer, 17.9 g), phosporus oxychloride (6.8 ml), N,N-dimethylformamide (5.5 ml), water (100 ml), acetone (50 ml.) and tetrahydrofuran (44 ml) were treated in a similar manner to that of Example 25 (1) to give 7-(2-methoxyimino-3,3-diethoxy-4-bromobutyramido)-3-hydroxycepham-4-carboxylic acid (syn isomer, 17.1 g.). The I.R. spectrum and N.M.R. spectrum of the compound were the same as those of Example 28.

EXAMPLE 30

Preparation of 2-methoxyimino-3,3-trimethylenedioxy-4-bromobutyric acid (syn isomer)

(1) Ethyl 2-methoxyimino-3-oxobutyrate (syn isomer, 10 g), 1,3-propanediol (11 g) and p-toluenesulfonic acid (300 mg) in dry benzene (150 ml) were treated in a similar manner to that of Example 1 (1) to give ethyl 2-methoxyimino-3,3-trimethylenedioxybutyrate (sun isomer, 4.46 g), bp 90°–95° C./0.8 mmHg.

I.R. (film): 3000, 2950, 2900, 2830, 1850, 1630, 1480, 1460, 1380 cm$^{-1}$

N.M.R. δ(CCl$_4$, ppm): 1.26 (3H, t, J=8 Hz), 1.44 (3H, s), 1.8–2.2 (2H, broad m), 3.6–4.0 (4H, m), 3.88 (3H, s), 4.2 (2H, q, J=8 Hz)

(2) Pyridium hydrobromide perbromide (3.32 g), and ethyl 2-methoxyimino-3,3-trimethylenedioxybutyrate (syn isomer, 2.0 g) in dry tetrahydrofuran (20 ml) were treated in a similar manner to that of Example 8 (2) to give ethyl 2-methoxyimino-3,3-trimethylenedioxy-4-bromobutyrate (syn isomer, 3.64 g).

I.R. (film): 3400, 2950–2850, 1730, 1620, 1460, 1440, 1370, 1280–1240, 1210, 1190, 1140, 1080, 1020 cm$^{-1}$ N.M.R. δ(CDCl$_3$, ppm): 1.30 (3H, t, J=7 Hz), 1.50–2.0 (2H, m), 3.4 (2H, t, J=6 Hz), 3.92 (3H, s), 4.28 (2H, q, J=7 Hz), 3.53 (2H, s), 3.61 (2H, t, J=6 Hz) (3) Ethyl 2-methoxyimino-3,3-trimethylenedioxy-4-bromobutyrate (syn isomer, 3.40 g) in ethanol (20.4 ml) and sodium hydroxide (1.32 g) in water (13.6 ml) were treated in a similar manner to that of Example 5 (2) to give 2-methoxyimino-3,3-trimethylenedioxy-4-bromobutyric acid (syn isomer, 1.68 g).

I.R. (Nujol): 3400–2200, 1750, 1620, 1470, 1430, 1380, 1300, 1260, 1240, 1230, 1200, 1140, 1080, 1030, 1000 cm$^{-1}$ N.M.R. δ(CDCl$_3$, ppm): 1.16–1.8 (2H, broad m), 3.58 (2H, s), 3.83–4.17 (4 H, m), 4.00 (3H, s).

EXAMPLE 31

2-Methoxyimino-3,3-trimethylenedioxy-4-bromobutyric acid (syn isomer) was treated in a similar manners to those of Example 25 (1) to (2) to give 7-(2-methoxyimino-3-oxo-4-bromobutyramido)-3-hydroxycepham-4-carboxylic acid (syn isomer).

EXAMPLE 32

7-(2-Methoxyimino-3-oxo-4-bromobutyramido)-3-hydroxy-cepham-4-carboxylic acid (syn isomer) was obtained in a similar manner to that of Example 10 (4) or Example 25 (2) by treating 7-(2-methoxyimino-3,3-dimethoxy-4-bromobutyramido)-3-hydroxycepham-4-carboxylic acid (syn isomer) or 7-(2-methoxyimino-3,3-diethoxy-4-bromobutyramido)-3-hydroxycepham-4-carboxylic acid (syn isomer).

EXAMPLE 33

(1) Acetic anhydride (22.5 ml.) and boron trifluoride etherate (7.5 ml.) were added to a stirred solution of 7-(2-methoxyimino-3-oxo-4-bromobutyramido)-3-hydroxycepham-4-carboxylic acid (syn isomer 31.8 g.) in dry tetrahydrofuran (150 ml.) at room temperature, and stirred at the same temperature for 30 minutes and at 50° C. for an hour. To the resultant solution was added a saturated aqueous solution of sodium chloride (100 ml.) and stirred for 30 minutes. Ethyl acetate (150 ml.) was added to the solution, and the ethyl acetate layer was separated, and washed with a saturated aqueous solution of sodium chloride.

The aqueous layer was extracted with ethyl acetate (100 ml.). The ethyl acetate layer and the extract were combined, treated with activated charcoal and evaporated. After adding diisopropyl ether (500 ml.) to the residue, the solvent was decanted. The residue was pulverized with diisopropyl ether, and the precipitates were collected by filtration and dried to give 7-(2-methoxyimino-3-oxo-4-bromobutyramido)-3-acetoxycepham-4-carboxylic acid (syn isomer, 35.3 g.)

I.R. (Nujol): 3250, 1710–1770, 1665, 1220 cm$^{-1}$

N.M.R. δ(DMSO-d$_6$, ppm): 2.02 (3H, s), 2.68–3.45 (2H, m), 3.95–4.15 (1H, m), 4.01 (3H, s), 4.56 (2H, s), 4.45–4.66 (1H, m), 5.19 (1H, d, J=2.1 Hz), 5.46 (1H, q, J=2.1 Hz, 4.0 Hz), 9.33 (2H, d, J=4.0 Hz) (2) Acetic anhydride (0.2 ml.), sodium acetate (0.12 g.) and N,N-dimethylformamide (2 drops) were added to a solution of 7-(2-methoxyimino-3-oxo-4-bromobutyramido)-3-acetoxy-cepham-4-carboxylic acid (syn isomer, 200 mg.) in dry tetrahydrofuran (2 ml), and stirred at 28° C. for an hour.

6 N Hydrochloric acid (0.2 ml.) was added to the resultant solution and the solvent was evaporated in vacuo. Water was added to the residue. The precipitates were collected by filtration, washed with water and dried to give a mixture (0.09 g.) of 7-(2-methoxyimino-3-oxo-4-bromobutyramido)-3-cephem-4-carboxylic acid (syn isomer) and 7-(2-methoxyimino-3-oxo-4-chlorobutyramido)-3-cephem-3-carboxylic acid (syn isomer). [7-(2-methoxyimino-3-oxo-4-bromobutyramido)-3-cephem-4-carboxylic acid (syn isomer)]

I.R. (Nujol): 3600–2200, 3240, 1780, 1700, 1690(sh), 1650, 1620, 1590, 1540, 1280, 1230(sh), 1210, 1050 cm$^{-1}$ N.M.R. δ(DMSO-d$_6$, ppm): 3.57 (2H, d, J=4 Hz), 4.57 (2H, s), 4.05 (3H, s), 5.05 (1H, d, J=5 Hz), 5.78 (1H, dd, J=5 Hz, 8 Hz), 6.50 (1H, s), 9.63 (1H, d, J=8 Hz)

EXAMPLE 34

Ethyl orthoformate (14.0 g) and borontrifluoride diethyletherate (0.45 g) were added to a solution of methyl 2-methoxyimino-3-oxobutyrate (syn isomer, 10 g) in ethanol (20 ml) and stirred at 70° C. for 4 hours. To the resultant mixture were added a saturated aqueous solution of sodium bicarbonate (20 ml) and diisopropyl ether (30 ml). After separating the organic solution, the aqueous solution was extracted with diisopropyl ether (30 ml). The organic layer and the extract were combined, washed with water and a saturated aqueous solution of sodium chloride (30 ml) in turn and dried over magnesium sulfate. The solution was evaporated in vacuo to give methyl 2-methoxyimino-3,3-diethoxybutyrate (syn isomer, 13.9 g).

I.R. (film): 2980, 2940, 2900, 2830, 1750, 1640, 1490, 1440, 1400, 1380, 1300, 1250, 1170, 1130, 1100, 1080, 1060–1030 cm$^{-1}$ N.M.R. δ(CDCl$_3$, ppm): 1.17 (6H, t, J=7 Hz), 1.60 (3H, s), 3.90 (3H, s), 3.55 (4H, q, J=7 Hz), 3.83 (3H, s)

EXAMPLE 35

Anhydrous potassium carbonate (8.89 g) was added to a solution of methyl 2-methoxyimino-3,3-diethoxybutyrate (syn isomer, 10 g) in chloroform (40 ml). Sulfuryl chloride (6.94 g) was added to the suspension at −6 to −2° C. over 50 minutes, and stirred at −5° to −2° C. for 10 minutes. After removing the solvent from the resultant mixture, ethanol (10 ml) was added to the residue and stirred for 30 minutes. Water (25 ml) was added to the mixture, and the mixture was extracted with diisopropyl ether (20 ml) twice. The extract was washed with water (10 ml) and a saturated aqueous solution of sodium chloride (5 ml) subsequently, and dried over magnesium sulfate. The solution was evaporated in vacuo to give methyl 2-methoxyimino-3,3-diethoxy-4-chlorobutyrate (syn isomer, 11.23 g).

I.R. (film): 2980, 2940, 2900, 2830, 1750, 1705, 1630, 1600, 1490, 1440, 1400, 1375, 1320, 1280, 1260, 1210, 1150, 1130, 1110, 1070–1030 cm$^{-1}$ N.M.R. δ(CDCl$_3$, ppm): 3.82 (2H, s), 1.18 (6H, t, J=7 Hz), 3.94 (3H, s), 3.11 (4H, q, J=7 Hz), 3.87 (3H, s)

EXAMPLE 36

Ethyl 2-methoxyimino-3,3-diethoxybutyrate (syn isomer, 10 g) was treated in a similar manner to that of Example 35 to give ethyl 2-methoxyimino-3,3-diethoxy-4-chlorobutyrate (syn isomer, 21.6 g).

I.R. (film): 2995, 2950, 2830, 2810, 1750, 1630, 1470, 1465, 1400, 1380, 1310, 1285, 1260, 1210, 1160, 1130, 1110, 1060, 1040 cm$^{-1}$ N.M.R. δ(CDCl$_3$, ppm): 1.18 (6H, t, J=6 Hz), 1.29 (3H, t, J=6 Hz), 3.56 (4H, q, J=6 Hz), 3.75 (2H, s), 3.88 (3H, s), 4.27 (2H, q, J=6 Hz)

EXAMPLE 37

A solution of sodium hydroxide (4.3 g) in water (20 ml) was added to a solution of ethyl 2-methoxyimino-3,3-diethoxy-4-chlorobutyrate (syn isomer, 10 g) in ethanol (30 g.), and stirred at 50° C. for 3 hours. The resultant solution was adjusted to pH 7.5 with 20% sulfuric acid, and evaporated ethanol from the solution. After adding diethyl ether (100 ml) to the solution under ice-cooling, the solution was adjusted to pH 2.5 with 20% sulfuric acid. The diethyl ether layer was separated and the aqueous layer was extracted with diethyl ether (50 ml). The organic layer and the extract were combined and washed with a saturated aqueous solution of sodium chloride, and dried over magnesium sulfate. The solution was evaporated in vacuo to give the residue (8.71 g). The residue was pulverized with n-hexane to give the powder of 2-methoxyimino-3,3-diethoxy-4-chlorobutyric acid (syn isomer, 6.47 g.).

I.R. (Nujol): 3240, 2970–2850, 1750, 1640, 1600, 1470, 1460, 1410, 1380, 1300, 1280, 1195, 1130, 1115, 1110, 1070–1010 cm$^{-1}$ N.M.R. δ(CDCl$_3$, ppm): 1.19 (6H, t, J=7 Hz), 3.63 (4H, q, J=7 Hz), 3.83 (2H, s), 3.98 (3H, s), 10.10 (1H, broad s)

EXAMPLE 38

Methyl 2-methoxyimino-3,3-diethoxy-4-chlorobutyrate (syn isomer, 4.83 g) was treated in a similar manner to that of Example 37 to give 2-methoxyimino-3,3-diethoxy-4-chlorobutyric acid (syn isomer, 3.83 g).

I.R. (Nujol): 3240, 2970–2850, 1750, 1640, 1600, 1470, 1460, 1410, 1380, 1280, 1195, 1130, 1115, 1110, 1070–1010 cm$^{-1}$ N.M.R. δ(CDCl$_3$, ppm): 1.19 (6H, t, J=7 Hz), 3.63 (4H, q, J=7 Hz), 3.83 (2H, s), 3.98 (3H, s), 10.10 (1H, broad s)

EXAMPLE 39

Phosphorus oxychloride (1.24 ml) was added to a solution of dry N,N-dimethylformamide (1.01 ml) in dry tetrahydrofuran (2ml ) at −20° C. and stirred at the same temperature for 30 minutes. To the solution was added 2-methoxyimino-3,3-diethoxy-4-bromobutyric acid (syn isomer, 3.3 g) at −20° C. and stirred at −20° to −10° C. for an hour. The resultant solution was added to a solution of potassium dihydrogenphosphate (3.63 g) and sodium phosphate (14.33 g) in water (1000 ml) and stirred under ice-cooling at pH 6.1 for 2 hours. The precipitates were collected by filtration, washed with water and dried to give 2-methoxyimino-3,3-diethoxy-4-bromobutyryl chloride (syn isomer, 3.0 g), mp 33°–35° C.

I.R. (Nujol): 1780, 1620, 1400, 1290, 1245, 1210, 1200 (sh), 1140 cm$^{-1}$

N.M.R. δ(CDCl$_3$, ppm): 1.2 (6H, t, J=7 Hz), 3.6 (4H, q, J=7 Hz), 3.70 (2H, s), 4.0 (3H, s)

EXAMPLE 40

2-Methoxyimino-3,3-diethoxy-4-chlorobutyric acid (syn isomer, 2.54 g) was treated in a similar manner to that of Example 39. The resultant mixture was extracted with n-hexane (200ml).

The extract was washed with water and a saturated aqueous solution of sodium chloride subsequently, dried over magnesium sulfate and concentrated in vacuo to give 2-methoxyimino-3,3-diethoxy-4-chlorobutyryl chloride (syn isomer, 2.58 g).

I.R. (film): 2990, 2950, 2910, 1800, 1620, 1490, 1470, 1460, 1445, 1405, 1300, 1220, 1200, 1140, 1120, 1100, 1060 cm$^{-1}$ N.M.R. δ(CCl$_4$, ppm): 1.18 (6H, t, J=7 Hz), 3.57 (2H, q, J=7 Hz), 3.68 (2H, s), 3.98 (3H, s)

EXAMPLE 41

Methanol (40 ml) was added to a solution of 7-amino-3-hydroxycepham-4-carboxylic acid (2 g) and sodium bicarbonate (0.57 g) in water (13.4 g) under ice-cooling. A solution of 2-methoxyimino-3,3-diethoxy-4-chlorobutyryl chloride (syn isomer, 1.34 g) in dry tetrahydrofuran (2 ml) was added to a solution while adjusting pH 6.5 to 7.8, then and stirred under ice-cooling for three hours. After adjusting the resultant mixture to pH 7.5, the solvent was removed in vacuo. The aqueous residue was adjusted to pH 7.5 under ice-cooling, and diisopropyl ether (10 ml) was added to the solution. After the aqueous solution was separated, ethyl acetate (20 ml) was added to the aqueous solution, and adjusted to pH 2.0 with 20% sulfuric acid. The ethyl acetate layer was separated and the aqueous solution was extracted with ethyl acetate (10 ml) twice. The ethyl acetate layer and the extract were combined, washed with a saturated aqueous solution of sodium chloride and dried over magnesium sulfate. The solution was concentrated in vacuo to give 7-(2-methoxyimino-3,3-diethoxy-4-chlorobutyramido)-3-hydroxycephem-4-carboxylic acid (syn isomer, 2.97 g).

N.M.R $\delta$(DMSO-$d_6$, ppm): 1.12 (6H, t, J=8 Hz), 2.6–3.2 (3H, m), 3.51 (4H, q, J=8 Hz), 3.80 (3H, s), 4.35 (1H, d, J=6 Hz), 5.08 (1H, d, J=5 Hz), 5.39 (1H, dd, J=5 Hz, 9 Hz), 8.61 (1H, d, J=9 Hz)

EXAMPLE 42

2-Methoxyimino-3,3-diethoxy-4-bromobutyryl chloride (syn isomer, 400.5 g) and 7-amino-3-hydroxycepham-4-carboxylic acid (230 g) were treated in a similar manner to that of Example 41 to give 7-(2-methoxyimino-3,3-diethoxy-4-bromobutyramido)-3-hydroxycepham-4-carboxylic acid (syn isomer, 621 g).

I.R. (film): 3600-3100 (broad), 2950, 1780-1700, 1520, 1380, 1040 (broad) cm$^{-1}$ N.M.R. $\delta$(DMSO-$d_6$, ppm): 1.12 (6H, t, J=7 Hz), 3.57 (4H, q, J=7 Hz), 2.62–3.93 (3H, m), 3.77 (2H, s), 3.90 (3H, s), 4.42 (1H, d, J=6 Hz), 5.13 (1H, d, J=4 Hz), 5.45 (1H, dd, J=4 Hz, 8 Hz), 8.60 (1H, d, J=8 Hz)

EXAMPLE 43

Acetic anhydride (27.3 ml) was added to a solution of 7-(2-methoxyimino-3,3-diethoxy-4-bromobutyramido)-3-hydroxycepham-4-carboxylic acid (syn isomer, 30 g) in dry tetrahydrofuran (300 ml) at room temperature and stirred at 28° C. for 30 minutes. After adding sodium acetate (4.0 g) and potassium acetate (4.7 g) to the solution, the solution was stirred at 28° to 30° C. for 3 hours. The resultant solution was added to a solution of ethyl acetate (300 ml) and a saturated aqueous solution of sodium chloride (300 ml), and adjusted to pH 2.0 with 20% sulfuric acid. After separating the organic layer, the aqueous layer was extracted with ethyl acetate (100 ml) twice. The organic layer and the extract were combined, washed with a saturated aqueous solution of sodium chloride, and then dried over magnesium sulfate. After treating the solution with activated charcoal, the solution was evaporated in vacuo. n-Hexane was added to the residue and decanted to give the oil (35.1 g) of 7-(2-methoxyimino-3,3-diethoxy-4-bromobutyramido)-3-cephem-4-carboxylic acid (syn isomer).

I.R. (film): 3500-2200 (broad), 3000, 2950, 2900, 1800-1650 (broad), 1540, 1380, 1300, 1130, 1050 cm$^{-1}$ N.M.R. $\delta$(DMSO-$d_6$, ppm): 1.17 (6H, t, J=7 Hz), 3.47–3.70 (2H, broad m), 3.57 (4H, q, J=7 Hz), 3.73 (2H, s), 3.93 (3H, s), 5.07 (1H, d, J=4 Hz), 6.78 (1H, dd, J=4 Hz, 8 Hz), 6.47 (1H, t, J=4 Hz), 8.80 (1H, d, J=8 Hz)

EXAMPLE 44

7-(2-Methoxyimino-3,3-diethoxy-4-chlorobutyramido)-3-hydroxycepham-4-carboxylic acid (syn isomer, 2.0 g) was treated in a similar manner to that of Example 43 to give 7-(2-methoxyimino-3,3-diethoxy-4-chlorobutyramido)-3-cephem-4-carboxylic acid (sym isomer, 1.87 g).

N.M.R. $\delta$(DMSO-$d_6$, ppm): 1.13 (3H, t, J=7 Hz), 3.6 (4H, q, J=7 Hz), 3.33–3.83 (2H, broad m), 3.87 (3H, s), 3.92 (2H, s), 5.08 (1H, d, J=5 Hz), 5.8 (1H, dd, J=5 Hz, 8 Hz), 6.5 (1H, t, J=5 Hz), 8.93 (1H, d, J=8 Hz)

EXAMPLE 45

7-(2-Methoxyimino-3,3-diethoxy-4-bromobutyramido)-3-hydroxycepham-4-carboxylic acid (syn isomer, 5 g), acetic anhydride (4.55 ml), sodium acetate (1.45 g), and methyl isobutyl ketone (50 ml) were treated in a similar manner to that of Example 43 to give 7-(2-methoxyimino-3,3-diethoxy-4-bromobutyramido)-3-cephem-4-carboxylic acid (syn isomer, 3.36 g).

I.R. (film): 3500-2200 (broad), 3000, 2950, 2900, 1800-1650 (broad), 1540, 1380, 1300, 1130, 1050 cm$^{-1}$ N.M.R. $\delta$(DMSO-$d_6$, ppm): 1.17 (6H, t, J=7 Hz), 3.47–3.70 (2H, broad m), 3.57 (4H, q, J=7 Hz), 3.73 (2H, s), 3.93 (3H, s), 5.07 (1H, d, J=4 Hz), 6.78 (1H, dd, J=4 Hz, 8 Hz), 6.47 (1H, t, J=4 Hz), 8.80 (1H, d, J=8 Hz)

EXAMPLE 46

70% Perchloric acid (3.4 ml) was added to a solution of 7-(2-methoxyimino-3,3-diethoxy-4-bromobutyramido)-3-hydroxycepham-4-carboxylic acid (syn isomer, 5.0 g) in acetone (40 ml) under ice-cooling and stirred at the same temperature for an hour. The precipitates were collected by filtration, washed with acetone (5 ml) twice and dried to give 7-(2-methoxyimino-3-oxo-4-bromobutyramido)-3-hydroxycepham-4-carboxylic acid (syn isomer, 1.85 g).

I.R. (Nujol)- 3460, 3280, 3200-2200, 1780, 1730, 1710, 1660, 1590, 1560, 1240, 1060 cm$^{-1}$ N.M.R. $\delta$(DMSO-$d_6$, ppm): 2.67–4.17 (3H, m), 4.08 (3H, s), 4.50 (1H, d, J=6 Hz), 4.67 (2H, s), 5.20 (1H, d, J=4 Hz), 5.53 (1H, d.d., J=4 Hz, 8 Hz), 9.40 (1H, d, J=8 Hz).

The mother liquid and the washing solution were combined and water (16 ml) was added thereto.

After adjusting to pH 2.0 with a saturated aqueous solution of sodium carbonate, acetone was removed in vacuo. A saturated aqueous solution of sodium chloride (16 ml) was added to the aqueous residue and allowed to stand in refrigerator overnight. The precipitates were collected by filtration, washed with a saturated aqueous solution of sodium chloride and water subsequently and dried to give the mixture of the above compound and 7-(2-methoxyimino-3-oxo-4-chlorobutyramido)-3-hydroxycepham-4-carboxylic acid (syn isomer, 1.35 g).

I.R. (Nujol): 3450, 3250, 3050, 1765, 1710, 1650, 1590, 1550, 1460, 1400, 1380, 1230, 1060 cm$^{-1}$ N.M.R. $\delta$(DMSO-$d_6$, ppm): 2.3–3.6 (2H, m), 3.6–4.0 (1H, broad s), 4.05 (3H, s), 4.33 (1H, d, J=6 Hz), 4.83 (2H, s), 5.17 (1H, d, J=4 Hz), 5.50 (1H, dd, J=4 Hz, 8 Hz), 9.33 (1H, d, J=8 Hz)

EXAMPLE 47

70% Perchloric acid (0.54 ml) was added to a solution of 7-(2-methoxyimino-3,3-diethoxy-4- bromobutyramido)-3-cephem-4-carboxylic acid (syn isomer, 1 g) in methyl isobutyl ketone (4 ml) under ice-cooling, and stirred at the same temperature for 20 minutes. Water (4 ml) was added to the resultant mixture and stirred for 5 minutes. The precipitates were collected by filtration, washed with water and dried over phosphorus pentachloride in vacuo to give 7-(2-methoxyimino-3-oxo-4-bromobutyramido)-3-cephem-4-carboxylic acid (syn isomer, 502 mg).

I.R. (Nujol): 3600-2200, 3240, 1780, 1700, 1690 (sh), 1650, 1620, 1590, 1540, 1280, 1230 (sh), 1210, 1050 cm$^{-1}$ N.M.R. $\delta$(DMSO-d$_6$, ppm): 3.57 (2H, d, J=4 Hz), 4.57 (2H, s), 4.05 (3H, s), 5.05 (1H, d, J=5 Hz), 5.78 (1H, dd, J=5 Hz, 8 Hz), 6.50 (1H, t, J=4 Hz), 9.63 (1H, d, J=8 Hz)

EXAMPLE 48

6 N Hydrochloric acid (2 ml) was added to a solution of 7-(2-methoxyimino-3,3-diethoxy-4-bromobutyramido)-3-hydroxycepham-4-carboxylic acid (syn isomer, 500 mg) in methylene chloride (5 ml) under ice-cooling and stirred at room temperature for 70 minutes. The precipitates were collected by filtration, washed with a saturated aqueous solution of sodium chloride (5 ml) and methylene chloride (1 ml) successively, and dried over phosphorus pentachloride to give 7-(2-methoxyimino-3-oxo-4-bromobutyramido)-3-hydroxycepham-4-carboxylic acid (syn isomer, 517 mg), purity: 57.8%.

I.R. (Nujol): 3460, 3280, 3200-2200, 1780, 1730, 1710, 1660, 1590, 1560, 1240, 1060 cm$^{-1}$ N.M.R. $\delta$(DMSO-d$_6$, ppm): 2.67-4.17 (3H, m), 4.08 (3H, s), 4.50 (1H, d, J=6 Hz), 4.67 (2H, s), 5.20 (1H, d, J=4 Hz), 5.53 (1H, dd, J=4 Hz, 8 Hz), 9.40 (1H, d, J=8 Hz).

EXAMPLE 49

7-(2-Methoxyimino-3,3-diethoxy-4-bromobutyramido)-3-cephem-4-carboxylic acid (syn isomer, 500 mg) was treated in a similar manner to that of Example 48 to give 7-(2-methoxyimino-3-oxo-4-bromobutyramido)-3-cephem-4-carboxylic acid (syn isomer, 250 mg), purity: 85.7%.

I.R. (Nujol): 3600-2200, 3240, 1780, 1700, 1690 (sh), 1650, 1620, 1590, 1540, 1280, 1230 (sh), 1210, 1050 cm$^{-1}$ N.M.R. $\delta$(DMSO-d$_6$, ppm): 3.57 (2H, d, J=4 Hz), 4.57 (2H, s), 4.05 (3H, s), 5.05 (1H, d, J=5 Hz), 5.78 (1H, dd, J=5 Hz, 8 Hz), 6.50 (1H, t, J=4 Hz), 9.63 (1H, d, J=8 Hz)

EXAMPLE 50

70% Perchloric acid (0.75 ml), 7-(2-methoxyimino-3,3-diethoxy-4-chlorobutyramido)-3-cephem-4-carboxylic acid (syn isomer, 1.82 g) and methyl isobutyl ketone (7.3 ml) were treated in a similar manner to that of Example 47 to give 7-(2-methoxyimino-3-oxo-4-chlorobutyramido)-3-cephem-4-carboxylic acid (syn isomer, 0.98 g).

I.R. (Nujol): 3250, 3050, 1780, 1710, 1650, 1620, 1590, 1550, 1280, 1230, 1060 cm$^{-1}$ N.M.R. (DMSO-d$_6$, ppm): 3.60 (2H, d, J=5 Hz), 4.07 (3H, s), 4.83 (2H, s), 5.10 (1H, d, J=4 Hz), 5.83 (1H, dd, J=4 Hz, 8 Hz), 6.53 (1H, t, J=5 Hz), 9.43 (1H, d, J=8 Hz)

EXAMPLE 51

6 N Hydrochloric acid (2.4 ml), 7-(2-methoxyimino-3,3-diethoxy-4-chlorobutyramido)-3-cephem-4-carboxylic acid (syn isomer, 301.5 mg) and methlene chloride (3 ml) were treated in a similar manner to that of Example 48 to give 7-(2-methoxyimino-3-oxo-4-chlorobutyramido)-3-cephem-4-carboxylic acid (syn isomer, 110.4 mg).

I.R. (Nujol): 3250, 3050, 1780, 1710, 1650, 1620, 1590, 1550, 1280, 1230, 1060 cm$^{-1}$ N.M.R. (DMSO-d$_6$, ppm): 3.60 (2H, d, J=5 Hz), 4.07 (3H, s), 4.83 (2H, s), 5.10 (1H, d, J=4 Hz), 5.83 (1H, dd, J=4 Hz, 8 Hz), 6.53 (1H, t, J=5 Hz), 9.43 (1H, d, J=8 Hz)

Thus obtained 7-(2-methoxyimino-3-oxo-4-chlorobutyramido)-3-cephem-4-carboxylic acid (syn isomer) was treated in a similar manner to that of Example 10-(10) to give 7-[2-(2-aminothiazol-4-yl)-2-methoxyiminoacetamido]-3-cephem-4-carboxylic acid (syn isomer).

What is claimed is:

1. A new compound of the formula:

$$X'-CH_2-C-C-COOH \quad (I)$$

with $A^1$—$A^2$ linked via O—O above the central carbon, and $\|N-OR^1$ on the adjacent carbon.

wherein
R$^1$ is an aliphatic hydrocarbon group which may have suitable substituent(s),
A$^1$ and A$^2$ are each lower alkyl or A$^1$ and A$^2$ are linked together to form lower alkylene and
X' is hydrogen or halogen, or its acid halide or its salt.

2. The compound of claim 1, which is 2-methoxyimino-3,3-ethylenedioxybutyric acid (syn isomer).

3. The compound of claim 1, which is 2-methoxyimino-3,3-ethylenedioxy-4-bromobutyric acid (syn isomer).

4. The compound of claim 1, which is 2-methoxyimino-3,3-ethylenedioxy-4-chlorobutyric acid (syn isomer).

5. The compound of claim 1, which is 2-methoxyimino-3,3-dimethoxy-4-bromobutyric acid (syn isomer).

6. The compound of claim 1, which is 2-methoxyimino-3,3-diethoxy-4-bromobutyryl chloride (syn isomer).

7. The compound of claim 1, which is 2-methoxyimino-3,3-diethoxy-4-chlorobutyryl chloride (syn isomer).

* * * * *

UNITED STATES PATENT AND TRADEMARK OFFICE
CERTIFICATE OF CORRECTION

PATENT NO. : 4,298,529
DATED : November 3, 1981
INVENTOR(S) : Ikuo Ueda et. al.

It is certified that error appears in the above-identified patent and that said Letters Patent are hereby corrected as shown below:

Please correct the Priority Data to read as follows:

[30]---Foreign Application Priority Data

Sep. 12, 1978 [JP]   Japan...................53-112555
    Sep. 12, 1978 [GB]   United Kingdom.........36564/78
    Jan. 12, 1979 [JP]   Japan...................54-3106
    Feb. 19, 1979 [GB]   United Kingdom.........5791/79 rather than

[30]---Foreign Application Priority Data

Sep. 12, 1978 [JP]   Japan...................53-112555
    Sep. 12, 1978 [GB]   United Kingdom.........36564/78
    Jan. 12, 1979 [JP]   Japan...................54-3106
    Sep. 12, 1978 [GB]   United Kingdom.........36564/78
    Feb. 19, 1979 [GB]   United Kingdom.........5791/79 as it now appears.

Signed and Sealed this

Second Day of February 1982

[SEAL]

*Attest:*

*Attesting Officer*

GERALD J. MOSSINGHOFF

*Commissioner of Patents and Trademarks*